(12) United States Patent
Maul et al.

(10) Patent No.: US 6,797,712 B2
(45) Date of Patent: Sep. 28, 2004

(54) SUBSTITUTED AMINO-FURAN-2-YL-ACETIC ACID AND AMINO-THIEN-2-YL-ACETIC ACID DERIVATIVES AND THEIR USE IN THE TREATMENT OF MIGRAINE AND PAIN

(75) Inventors: Corinna Maul, Aachen (DE); Werner Englberger, Stolberg (DE); Michael Przewosny, Aachen (DE)

(73) Assignee: Gruenenthal GmbH, Aachen (DE)

(*) Notice: Subject to any disclaimer, the term of this patent is extended or adjusted under 35 U.S.C. 154(b) by 0 days.

(21) Appl. No.: 10/448,323

(22) Filed: May 30, 2003

(65) Prior Publication Data
US 2004/0030156 A1 Feb. 12, 2004

Related U.S. Application Data

(63) Continuation of application No. PCT/EP01/13910, filed on Nov. 28, 2001.

(30) Foreign Application Priority Data

Nov. 30, 2000 (DE) .......................................... 100 59 864

(51) Int. Cl.[7] ........................ A61K 31/34; A61K 31/38; C07D 307/54; C07D 333/26
(52) U.S. Cl. ........................ 514/255; 514/275; 514/336; 514/403; 514/438; 514/471; 546/280.4; 546/283.4; 546/284.7; 544/331; 544/405; 548/364.1; 549/76; 549/486; 549/473; 549/496
(58) Field of Search .......................... 549/76, 486, 496, 549/473; 546/280.4, 283.4, 284.7; 548/364.1; 544/331, 405; 514/255, 275, 336, 403, 438, 471

(56) References Cited

U.S. PATENT DOCUMENTS 6,441,237 B1   8/2002   Stransky et al. ............. 564/362

FOREIGN PATENT DOCUMENTS

| DE | 19907385 A1 | 8/2000 | ......... C07C/217/48 |
| WO | WO 98/00398 | 1/1998 | ......... C07D/207/00 |
| WO | WO 01/96323 | 12/2001 | ......... C07D/295/18 |

OTHER PUBLICATIONS

Abstract XP–002192099 and attached article "Enantioselective Syntheses of α–, β–, and γ–Aryl Amino Acids and Esters", *J. Org. Chem.*, 1997, 62(6), pp. 1574–1575.

N. Petasis, et al., "A New Synthesis of α–Arylglycines from Aryl Boronic Acids" *Tetrahedron* (1997) p. 16463–16470.

P. Leeson et al., "The Glycine Site on the NMDA Receptor: Structure–Activity Relationships and Therapeutic Potential" *J. Med. Chem.*, 1994, 37(24), pp. 4053–4067.

*Primary Examiner*—Bernard Dentz
(74) *Attorney, Agent, or Firm*—Crowell & Moring LLP

(57) ABSTRACT

Compounds of formula I, or a pharmaceutically acceptable salt thereof,

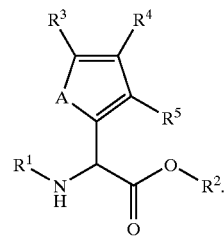

The compounds of the present invention are suitable for the treatment of pain and migraine. Also disclosed are method for preparing the compounds, and pharmaceutical composition comprising the compounds as well as methods for treating pain and migraine using the pharmaceutical compositions.

20 Claims, No Drawings

SUBSTITUTED AMINO-FURAN-2-YL-ACETIC ACID AND AMINO-THIEN-2-YL-ACETIC ACID DERIVATIVES AND THEIR USE IN THE TREATMENT OF MIGRAINE AND PAIN

CROSS REFERENCE TO RELATED APPLICATIONS

The present application is a continuation of International Patent Application No. PCT/EP01/13910, filed Nov. 28, 2001, designating the United States of America and published in German as WO 02/44171 A1, the entire disclosure of which is incorporated herein by reference. Priority is claimed based on Federal Republic of Germany Patent Application No. 100 59 864.1, filed Nov. 30, 2000.

FIELD OF THE INVENTION

The invention relates to substituted amino-furan-2-yl-acetic acid derivatives and substituted amino-thien-2-yl-acetic acid derivatives, to processes for their preparation, to medicaments containing them, to the use of those compounds in the preparation of medicaments for the treatment of, inter alia, pain and migraine, and to pharmaceutical compositions containing them.

BACKGROUND OF THE INVENTION

The treatment of chronic and non-chronic pain is of great importance in medicine. There is a worldwide need for highly effective therapies for the targeted treatment of chronic and non-chronic pain in a manner that is fair to the patient, which is understood to mean the successful and satisfactory treatment of pain for the patient.

Conventional opioids such as morphine are highly effective in the therapy of severe to the most severe pain. However, their use is limited by the known side-effects, such as respiratory depression, vomiting, sedation, constipation and tolerance. In addition, they are less effective in neuropathic or incidental pain, from which tumor patients in particular suffer.

Opioids develop their analgesic action by binding to receptors in the cell membrane which belong to the family of the so-called G-protein-coupled receptors. In addition, there are further receptors and also ion channels which are substantially involved in the system of pain formation and pain transmission, for example the N-methyl-D-aspartate ion channel (NMDA ion channel), via which a substantial part of the communication of synapses proceeds and through which the calcium ion exchange between a neuronal cell and its surroundings is controlled (see, for example, P. D. Leeson, L. L. Iversen, *J. Med. Chem.* 37 (1994) 4053–4067).

Important findings regarding the physiological importance of ion-channel-selective substances have been made possible by the development of the "patch-clamp" technique, by means of which the action of NMDA antagonists (i.e. antagonists of the NMDA ion channel) on the metabolism of calcium inside the cell can be demonstrated.

DESCRIPTION OF THE INVENTION

The object underlying the present invention is to provide novel compounds suitable for the therapy of pain. In addition, it is desirable that these substances have only minimal, if any, of the side-effects that usually occur with the use of opioids such as morphine, such as nausea, vomiting, dependence, respiratory depression or constipation.

That object is achieved by compounds having the general structure (I) and by their pharmaceutically acceptable salts:

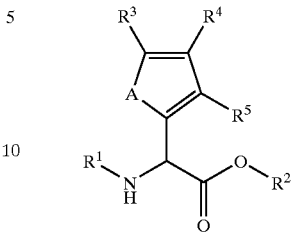

wherein

A represents oxygen or sulfur, $R^1$ represents aryl, ($C_{1-6}$-alkyl)-aryl, heterocyclyl or ($C_{1-6}$-alkyl)-heterocyclyl, $R^2$ represents H, $C_{1-12}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl or ($C_{1-6}$-alkyl)-heterocyclyl, $R^3$, $R^4$ and $R^5$ each independently of the others represents H, OH, SH, F, Cl, Br, I, —CN, $NO_2$, $C_{1-2}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl, ($C_{1-6}$-alkyl)-heterocyclyl, —$SiR^6R^7R^8$, —$(CH_2)_n$—O—$(CH_2)_m$—$R^9$ wherein n=1, 2, 3 or 4 and m=0, 1, 2, 3 or 4, —$(CH_2)_o$—$S_p$—$(CH_2)_q$—$R^{10}$ wherein o=1, 2, 3 or 4, p=1 or 2 and q=0, 1, 2, 3 or 4, —$(CH_2)_r$—$CO_2R^{11}$ wherein r=0, 1, 2, 3 or 4, —$(CH_2)_s$—$OCOR^{12}$ wherein s=0, 1, 2, 3 or 4, or —$COR^{13}$, $R^6$, $R^7$ and $R^8$ each independently of the others represents $C_{1-6}$-alkyl or phenyl, $R^9$ and $R^{10}$ each independently of the other represents H, $CH_3$, aryl, heterocyclyl or —C(=O)—$C_{1-6}$-alkyl, —C(=O)—($C_{1-6}$-alkyl)-aryl or —C(=O)-aryl, $R^{11}$ represents H, $C_{1-6}$-alkyl or $CH_2$-phenyl, $R^{12}$ represents $C_{1-6}$-alkyl or aryl, $R^{13}$ represents H, $C_{1-6}$-alkyl, aryl, heterocyclyl or $NR^{14}R^{15}$, $R^{14}$ and $R^{15}$ each independently of the other represents H, $C_{1-6}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl or ($C_{1-6}$-alkyl)-heterocyclyl, or $R^{14}$ and $R^{15}$ together form —$(CH_2)_k$— wherein k=4, 5 or 6, wherein alkyl represents a non-cyclic hydrocarbon radical which is straight-chain or branched and is saturated or unsaturated and is unsubstituted or is monosubstituted or polysubstituted by identical or different substituents, cycloalkyl represents an alicyclic hydrocarbon radical which is saturated or unsaturated and is unsubstituted or is monosubstituted or polysubstituted by identical or different substituents, aryl is a radical selected from the group of

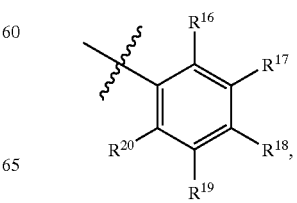

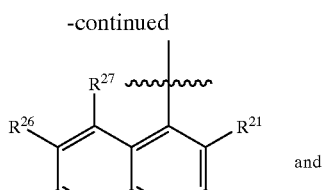

and

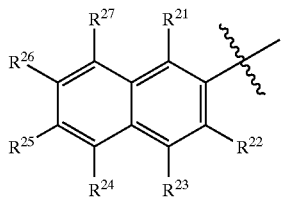

heterocyclyl represents a monocyclic or polycyclic organic radical in which at least one ring contains one hetero atom or 2, 3, 4 or 5 identical or different hetero atoms selected from the group of N, O and S, the radical being saturated or unsaturated and being unsubstituted or monosubstituted or polysubstituted by identical or different substituents, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ each independently of the others represents H, $OR^{28}$, $S(O)_tR^{29}$ wherein t=0, 1 or 2, $SO_2OR^{30}$, F, Cl, Br, I, —CN, $NO_2$, $C_{1-12}$-alkyl, $C_{3-8}$-cycloalkyl, $(C_{1-6}$-alkyl)-$C_{3-8}$-cycloalkyl, phenyl or $(C_{1-6}$-alkyl)-phenyl, wherein phenyl is unsubstituted or is monosubstituted or polysubstituted by identical or different substituents, heterocyclyl, $(C_{1-6}$-alkyl)-heterocyclyl, —$CO_2R^{31}$ or —$NR^{32}R^{33}$, $R^{28}$, $R^{29}$, $R^{30}$ and $R^{31}$ each independently of the others represents H, $C_{1-12}$-alkyl, $C_{3-8}$-cycloalkyl, $(C_{1-6}$-alkyl)-$C_{3-8}$-cycloalkyl, phenyl or $(C_{1-6}$-alkyl)-phenyl, wherein phenyl is unsubstituted or is monosubstituted or polysubstituted by identical or different substituents, heterocyclyl, $(C_{1-6}$-alkyl)-heterocyclyl or —$NR^{34}R^{35}$, and $R^{32}$ and $R^{33}$ each independently of the other represents H, $C_{1-6}$-alkyl, $C_{3-8}$-cycloalkyl, $(C_{1-6}$-alkyl)-$C_{3-8}$-cycloalkyl, phenyl, $(C_{1-6}$-alkyl)-phenyl, heterocyclyl or $(C_{1-6}$-alkyl)-heterocyclyl, or $R^{32}$ and $R^{33}$ together form —$(CH_2)_h$— wherein h=4, 5 or 6, and $R^{34}$ and $R^{35}$ each independently of the other represents H, $C_{1-6}$-alkyl, $C_{3-8}$-cycloalkyl, $(C_{1-6}$-alkyl)-$C_{3-8}$-cycloalkyl, phenyl, $(C_{1-6}$-alkyl)-phenyl, heterocyclyl or $(C_{1-6}$-alkyl)-heterocyclyl, or $R^{34}$ and $R^{35}$ together form —$(CH_2)_g$— wherein g=4, 5 or 6.

Accordingly, the compounds according to the invention having the general structure (I) are either amino-furan-2-yl-acetic acid derivatives having the general structure (I-A) or amino-thien-2-yl-acetic acid derivatives having the general structure (I-B):

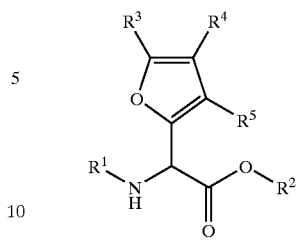

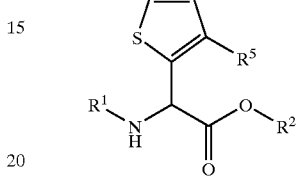

It has been found that the compounds having the general structure (I-A) or (I-B) bind selectively to the glycine binding site of the NMDA ion channel and accordingly are suitable for the treatment of pain. The same is also true of (4-methoxy-phenylamino)-thien-2-yl-acetic acid, which is known as such from the prior art (N. A. Petasis et al., *Tetrahedron* (1997), 16463–16470) but for which no medicinal indication is disclosed in the prior art. The present invention therefore relates also to that compound, in so far as its use in a medicament, for the preparation of a medicament, especially for the treatment of pain, and a pharmaceutical composition containing it are concerned.

Within the scope of this invention, the term "aryl" means phenyls and naphthyls. Each aryl radical may be unsubstituted or mono- or poly-substituted, it being possible for the aryl substituents to be identical or different and to be at any desired and possible position of the aryl. Aryl is advantageously an unsubstituted or substituted phenyl. Particularly preferred aryl radicals for the purposes of the invention are mono- or di-substituted phenyl.

Within the scope of this invention, the terms "$C_{1-12}$-alkyl" and "$C_{1-6}$-alkyl" include acyclic saturated or unsaturated hydrocarbon radicals which may be branched- or straight-chain and may be unsubstituted or mono- or poly-substituted, having from 1 to 12 (i.e. 1, 2, 3, 4, 5, 6, 7, 8, 9, 10, 11 or 12) and from 1 to 6 (i.e. 1, 2, 3, 4, 5 or 6) carbon atoms, respectively, that is to say $C_{1-12}$-alkanyls and $C_{1-6}$-alkanyls, $C_{2-12}$-alkenyls and $C_{2-6}$-alkenyls and $C_{2-12}$-alkynyls and $C_{2-6}$-alkynyls. "Alkenyls" have at least one C—C double bond and "alkynyls" have at least one C—C triple bond. Alkyl is advantageously selected from the group of methyl, ethyl, n-propyl, 2-propyl, n-butyl, isobutyl, sec-butyl, tert-butyl, n-pentyl, isopentyl, neopentyl, n-hexyl, 2-hexyl, n-octyl, n-nonyl, n-decyl, n-dodecyl; ethenyl (vinyl), ethynyl, propenyl (—$CH_2CH=CH_2$, —CH=CH—$CH_3$, —C(=$CH_2$)—$CH_3$), propynyl (—$CH_2$—C≡CH, —C≡C—$CH_3$), butenyl, butynyl, pentenyl, pentynyl, hexenyl, hexynyl, octenyl and octynyl.

For the purposes of this invention, the term "$C_{3-8}$-cycloalkyl" means cyclic hydrocarbon radicals having 3, 4, 5, 6, 7 or 8 carbon atoms, it being possible for the radicals to be saturated or unsaturated, unsubstituted or monosubstituted or polysubstituted by identical or different substituents. $C_{3-8}$-Cycloalkyl is advantageously selected from the group of cyclopropyl, cyclobutyl, cyclopentyl, cyclohexyl, cycloheptyl, cyclooctyl, cyclopentenyl, cyclohexenyl, cycloheptenyl and cyclooctenyl.

The term "heterocyclyl" denotes a 3-, 4-, 5-, 6- or 7-membered cyclic organic radical which contains at least one hetero atom, optionally 2, 3, 4 or 5 hetero atoms, wherein the hetero atoms are identical or different and are selected from the group containing oxygen, nitrogen and sulfur, and the cyclic radical is saturated or unsaturated and may be unsubstituted or mono- or poly-substituted. The heterocycle may also be part of a bicyclic or polycyclic system; for example, a benzene ring may be fused to the heterocycle. Examples of preferred heterocyclyl radicals are furanyl, thienyl (thiophene), indolyl, imidazolyl, pyrazolyl, oxazolyl, isoxazolyl, pyridinyl, pyrimidinyl, pyrazinyl and their benzo-fused derivatives. The bond to the compound having the general structure (I) (or (II), (III) and (IV)) can be made via any desired and chemically possible ring member of the heterocyclyl radical.

For the purposes of the present invention, the expressions "($C_{1-6}$-alkyl)-$C_{3-8}$-cycloalkyl," "($C_{1-6}$-alkyl)-heterocyclyl" and "($C_{1-6}$-alkyl)-aryl" mean that the cycloalkyl, heterocyclyl or aryl radical is bonded to the compound having the general structure (I) (or (II), (III) or (IV)) via a $C_{1-6}$-alkyl group.

In connection with "alkyl," "alkanyl," "alkenyl" and "alkynyl," the term "substituted" within the scope of this invention is understood to mean the substitution of a hydrogen atom by, for example, F, Cl, Br, I, —CN, $NH_2$, NH-alkyl, NH-aryl, NH-alkyl-aryl, NH-heterocyclyl, NH-alkyl-OH, N(alkyl)$_2$, N(alkyl-aryl)$_2$, N(heterocyclyl)$_2$, N(alkyl-OH)$_2$, NO, $NO_2$, SH, S-alkyl, S-aryl, S-alkyl-aryl, S-heterocyclyl, S-alkyl-OH, S-alkyl-SH, OH, O-alkyl, O-aryl, O-alkyl-aryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl,

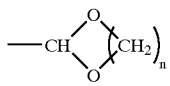

wherein n=1, 2 or 3, C(=S)$C_{1-6}$-alkyl-aryl, C(=O)-heterocyclyl, C(=S)-heterocyclyl, $CO_2H$, $CO_2$-alkyl, $CO_2$-alkyl-aryl, C(=O)$NH_2$, C(=O)NH-alkyl, C(=O)NHaryl, C(=O)NH-heterocyclyl, C(=O)N(alkyl)$_2$, C(=O)N(alkyl-aryl)$_2$, C(=O)N(heterocyclyl)$_2$, SO-alkyl, $SO_2$-alkyl, $SO_2$-alkyl-aryl, $SO_2NH_2$, $SO_3H$, $SO_3$-alkyl, cycloalkyl, aryl or by heterocyclyl; polysubstituted radicals being understood to be radicals that are polysubstituted, for example di- or tri-substituted, either at different atoms or at the same atom, for example trisubstituted at the same carbon atom, as in the case of $CF_3$ or —$CH_2CF_3$, or at different positions, as in the case of —CH(OH)—CH=CCl—$CH_2$Cl. Polysubstitution can be carried out with the same or with different substituents. For the purposes of the present invention, "alkyl" in this connection particularly preferably means methyl, ethyl, n-propyl, 2-propyl, n-butyl, 2-butyl, tert-butyl, $CH_2$—OH or $CF_3$.

With regard to "aryl," "phenyl," "heterocyclyl" and "cycloalkyl," "monosubstituted" or "polysubstituted" is understood to mean within the scope of this invention the mono- or poly-substitution, for example di-, tri- or tetra-substitution, of one or more hydrogen atoms of the ring system by a suitable substituent. If the meaning of such suitable substituents in connection with "aryl," "phenyl,"

"heterocyclyl" or "cycloalkyl" is not defined elsewhere in the description or in the claims, suitable substituents are F, Cl, Br, I, CN, $NH_2$, NH-alkyl, NH-aryl, NH-alkyl-aryl, NH-heterocyclyl, NH-alkyl-OH, N(alkyl)$_2$, N(alkyl-aryl)$_2$, N(heterocyclyl)$_2$, N(alkyl-OH)$_2$, NO, $NO_2$, SH, S-alkyl, S-cycloalkyl, S-aryl, S-alkyl-aryl, S-heterocyclyl, S-alkyl-OH, S-alkyl-SH, OH, O-alkyl, O-cycloalkyl, O-aryl, O-alkyl-aryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl,

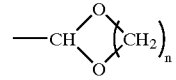

wherein n=1, 2 or 3, C(=S)$C_{1-6}$-alkyl-aryl, C(=O)-heterocyclyl, C(=S)-heterocyclyl, $CO_2H$, $CO_2$-alkyl, $CO_2$-alkyl-aryl, C(=O)$NH_2$, C(=O)NH-alkyl, C(=O)NHaryl, C(=O)NH-heterocyclyl, C(=O)N(alkyl)$_2$, C(=O)N(alkyl-aryl)$_2$, C(=O)N(heterocyclyl)$_2$, S(O)-alkyl, S(O)-aryl, $SO_2$-alkyl, $SO_2$-aryl, $SO_2NH_2$, $SO_3H$, $CF_3$, =O, =S; alkyl, cycloalkyl, aryl and/or heterocyclyl; at one atom or optionally at different atoms (it being possible for a substituent itself to be substituted). Polysubstitution is carried out with the same or with different substituents. When "aryl" represents phenyl, the phenyl ring is optionally substituted by one or more substituents $R^{16}$, $R^{17}$, $R^{18}$, $R^{19}$ and $R^{20}$ as defined above for the general structure (I).

Pharmaceutically acceptable salts within the scope of this invention are those salts of the compounds according to the invention having the general structure (I) which are physiologically tolerable when used pharmaceutically—especially when used in mammals and/or humans. Such pharmaceutically acceptable salts can be formed, for example, with inorganic or organic acids or, where the compounds according to the invention are acids, especially carboxylic acids, with bases.

The pharmaceutically acceptable salts of the compounds according to the invention having the general structure (I) are preferably formed with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. If the compounds according to the invention are acids, especially carboxylic acids, the pharmaceutically acceptable salts can also be formed by reaction with bases, such as sodium hydrogen carbonate or sodium carbonate. The salts formed are, inter alia, hydrochlorides, hydrobromides, phosphates, carbonates, hydrogen carbonates, formates, acetates, oxalates, succinates, tartrates, fumarates, citrates and glutamates, or sodium salts. Also preferred are solvates and, especially, the hydrates of the compounds according to the invention, which can be obtained, for example, by crystallization from aqueous solution.

The compounds according to the invention having the general structure (I) always have at least one center of asymmetry, which is denoted by * in the formula below:

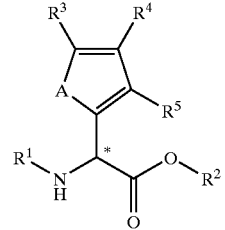

The compounds according to the invention of the general formula (I) can therefore be in the form of their racemates, in the form of the pure enantiomers and/or—provided a further center of asymmetry is present—in the form of the pure diastereoisomers, or in the form of mixtures of those enantiomers and diastereoisomers, both in the depicted form and in the form of pharmaceutically acceptable salts thereof. The mixtures may be present in any desired mixing ratio of the stereoisomers.

Preference is given to those compounds having the general structure (I) which are characterised in that $R^1$ represents aryl or heterocyclyl$^1$, $R^2$ represents H, $C_{1-12}$-alkyl, $(C_{1-6}$-alkyl)-$C_{3-8}$-cycloalkyl, aryl or $(C_{1-6}$-alkyl)-aryl, $R^3$, $R^4$ and $R^5$ each independently of the others represents H, OH, SH, Cl, Br, $C_{1-12}$-alkyl, $C_{3-8}$-cycloalkyl, $(C_{1-6}$-alkyl)-$C_{3-8}$-cycloalkyl, aryl, $(C_{1-6}$-alkyl)-aryl, heterocyclyl$^1$, $(C_{1-6}$-alkyl)-heterocyclyl$^1$, —SiR$^6$R$^7$R$^8$, —(CH$_2$)$_n$—O—(CH$_2$)$_m$—R$^9$ wherein n=1, 2, 3 or 4 and m=0, 1 or 2, —(CH$_2$)$_o$—S$_p$—(CH$_2$)$_q$—R$^{10}$ wherein o=1, 2, 3 or 4, p=1 or 2 and q=0, 1 or 2, —(CH$_2$)$_r$—CO$_2$R$^{11}$ wherein r=0, 1, 2 or 3, —(CH$_2$)$_s$—OCOR$^{12}$ wherein s=0, 1 or 2, or —COR$^{13}$, $R^6$, $R^7$ and $R^8$ each independently of the others represents $C_{1-6}$-alkyl or phenyl, $R^9$ and $R^{10}$ each independently of the other represents H, CH$_3$, aryl, heterocyclyl or —C(=O)—$C_{1-6}$-alkyl, —C(=O)—($C_{1-6}$-alkyl)-aryl or —C(=O)-aryl, $R^{11}$ represents H, $C_{1-6}$-alkyl or CH$_2$-phenyl, $R^{12}$ represents $C_{1-6}$-alkyl or aryl, $R^{13}$ represents $C_{1-6}$-alkyl or aryl,

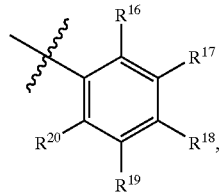

wherein aryl represents heterocyclyl represents a monocyclic or polycyclic organic radical in which at least one ring contains one hetero atom or 2, 3, 4 or 5 identical or different hetero atoms selected from the group of N, O and S, the radical being saturated or unsaturated and being unsubstituted or monosubstituted or polysubstituted by identical or different substituents, heterocyclyl$^1$ represents a monocyclic or bicyclic organic radical in which at least one ring is 5- or 6-membered and contains one hetero atom or 2 identical or different hetero atoms selected from the group of N, O and S, the radical being saturated or unsaturated and being unsubstituted or monosubstituted or polysubstituted by identical or different substituents, $R^{16}$, $R^{17}$, $R^{18}$, $R^{19}$ and $R^{20}$ each independently of the others represents H, OR$^{28}$, S(O)$_t$R$^{29}$ wherein t=0 or 2, SO$_2$OR$^{30}$, F, Cl, Br, I, —CN, NO$_2$, $C_{1-12}$-alkyl, $C_3$ g-cycloalkyl, $(C_{1-6}$-alkyl)-$C_{3-8}$-cycloalkyl, phenyl or $(C_{1-6}$-alkyl)-phenyl, wherein phenyl is unsubstituted or is monosubstituted or polysubstituted by identical or different substituents, heterocyclyl$^1$, $(C_{1-6}$-alkyl)-heterocyclyl$^1$, —CO$_2$R$^{31}$ or —NR$^{32}$R$^{33}$, $R^{28}$, $R^{29}$, $R^{30}$ and $R^{31}$ each independently of the others represents H, $C_{1-6}$-alkyl or phenyl, and $R^{32}$ and $R^{33}$ each independently of the other represents H, $C_{1-6}$-alkyl, $(C_{1-6}$-alkyl)-phenyl, or $R^{32}$ and $R^{33}$ together form —(CH$_2$)$_h$— wherein h=4, 5 or 6.

Of those compounds, particular preference is given to those in which $R^1$ represents aryl or heterocyclyl$^2$, $R^2$ represents H, methyl, ethyl, n-propyl, 2-propyl, n-butyl, tert-butyl, n-hexyl, $R^3$, $R^4$ and $R^5$ each independently of the others represents H, OH, SH, Br, Cl, $C_{1-6}$-alkyl, 2-furyl, 3-furyl, 2-thienyl, 3-thienyl, —SiR$^6$R$^7$R$^8$, —CH$_2$OH, —CH$_2$—O—(C=O)—CH$_3$, —(CH$_2$)—S$_p$—(CH$_2$)$_q$—R$^{10}$ wherein p=1 or 2 and q=0 or 1, —(CH$_2$)$_r$—CO$_2$R$^{11}$ wherein r=0 or 1, or —COR$^{13}$, $R^6$, $R^7$ and $R^8$ each independently of the others represents methyl, tert-butyl or phenyl, $R^{10}$ represents H, methyl, ethyl, 2-furyl, 2-thienyl or —C(=O)—CH$_3$, $R^{11}$ represents H, methyl, ethyl or tert-butyl, $R^{13}$ represents methyl,

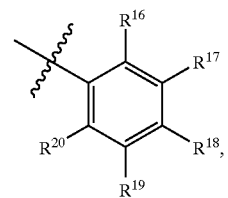

wherein aryl represents

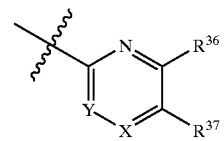 or 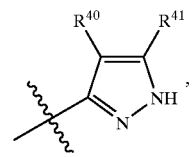

heterocyclyl$^2$ represents $R^{16}$, $R^{17}$, $R^{18}$, $R^{19}$ and $R^{20}$ each independently of the others represents H, OR$^{28}$, S(O)$_t$R$^{29}$ wherein t=0, F, Cl, Br, I, —CN, —NO$_2$, methyl, ethyl, n-propyl, 2-propyl, n-butyl, 2-butyl, isobutyl, tert-butyl, n-pentyl, neopentyl, isopentyl, n-hexyl, isohexyl, CF$_3$ or —CO$_2$R$^{31}$, $R^{28}$, $R^{29}$ and $R^{31}$ each independently of the others represents H, methyl, ethyl, —CF$_3$ or phenyl, X—Y represents CR$^{38}$—CR$^{39}$, CR$^{38}$—N or N—CR$^{39}$, $R^{36}$, $R^{37}$, $R^{38}$ and $R^{39}$ each independently of the others represents H, F, Cl, Br, I, —CN, —NO$_2$, —OH, —SH, $C_{1-6}$-alkyl or —CF$_3$, and $R^{40}$ and $R^{41}$ each independently of the other represents H, F, Cl, Br, I, —CN, —OH, —O-$C_{1-6}$-alkyl, —SH, —S—$C_{1-6}$-alkyl, $C_{1-8}$-alkyl, CO$_2$—$C_{1-6}$-alkyl or —N=N-aryl.

Very particularly preferred compounds having the general structure (I) are those which are characterised in that $R^1$ represents aryl or heterocyclyl$^2$, $R^2$ represents H, methyl, ethyl or tert-butyl, $R^3$ represents H, Cl, methyl, ethyl, n-propyl, 2-propyl, n-butyl, tert-butyl, —CH$_2$OH, —CH$_2$SH, —CH$_2$—S—CH$_3$, —CH$_2$—S—CH$_2$-furan-2-yl, —CH$_2$—O—(C=O)—CH$_3$, —CH$_2$—S—(C=O)—CH$_3$, —CH$_2$—S—S—CH$_3$, —CH$_2$—S—S—CH$_2$-furan-2-yl, —CH$_2$—CO$_2$methyl or —CH$_2$—CO$_2$ethyl, R⁴ represents H, Br, methyl, ethyl, —CH₂OH, —CO₂methyl, —CO₂ethyl or —COmethyl,
R⁵ represents H, methyl or ethyl,

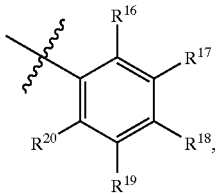

wherein aryl represents R

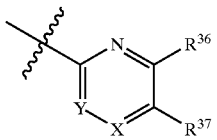 or 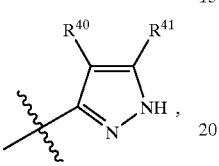

heterocyclyl² represents
R¹⁶ represents H, —O-phenyl, F, Cl, Br, methyl, ethyl, n-propyl, 2-propyl or tert-butyl,
R¹⁷ represents H, Cl, methyl, ethyl or CF₃,
R¹⁸ represents H, F, Cl, Br, I, —CN, —O—CH₃, —O—CF₃, —O-phenyl, methyl, ethyl, n-propyl, 2-propyl, n-butyl, 2-butyl or tert-butyl,
R¹⁹ represents H, Cl, Br, methyl or ethyl,
R²⁰ represents H or methyl,
X—Y represents CR³⁸—CR³⁹, CR³⁸—N or N—CR³⁹,
R³⁶ represents H, methyl or ethyl,
R³⁷ represents H, NO₂, Cl, Br, methyl or CF₃,
R³⁸ represents H,
R³⁹ represents H, Cl or Br,
R⁴⁰ represents H, —N=N-phenyl, —CN, CO₂H, CO₂-methyl or CO₂-ethyl, and
R⁴¹ represents H, OH, SH, S-methyl, methyl, ethyl, n-propyl, 2-propyl, n-butyl or tert-butyl.

Of those very particularly preferred compounds, special preference is given to those in which
R¹ represents 4-trifluoromethoxy-phenyl, 2-phenoxy-phenyl, 4-phenoxy-phenyl, 2-chloro-phenyl, 4-chloro-phenyl, 4-iodo-phenyl, 4-cyano-phenyl, 2-methyl-phenyl, 2-ethyl-phenyl, 4-ethyl-phenyl, 2-(2-propyl)-phenyl, 4-(2-butyl)-phenyl, 4-tert-butyl-phenyl, 2,4-dichlorophenyl, 2,3-dichlorophenyl, 3,5-dichlorophenyl, 2,4-dibromo-phenyl, 4-chloro-2-fluoro-phenyl, 2-chloro-4-fluoro-phenyl, 4-bromo-2-chloro-phenyl, 2-chloro-4-iodo-phenyl, 3-chloro-2-methyl-phenyl, 4-chloro-2-methyl-phenyl, 5-chloro-2-methyl-phenyl, 2-chloro-4-methyl-phenyl, 4-chloro-3-trifluoromethyl-phenyl, 2,4-dibromo-5-methyl-phenyl, 5-nitro-pyridin-2-yl, 3,5-dibromo-pyridin-2-yl, 3,5-dichloro-pyridin-2-yl, 3-chloro-5-trifluoromethyl-pyridin-2-yl, 3,5-dibromo-6-methyl-pyridin-2-yl, pyrazin-2-yl, 5-bromo-pyrimidin-2-yl, 4-carboxyethyl-pyrazol-3-yl, 4-cyano-pyrazol-3-yl, 5-tert-butyl-pyrazol-3-yl, 5-hydroxy-4-(4-phenylazo)-pyrazol-3-yl or 4-cyano-5-thiomethyl-pyrazol-3-yl,
R² represents H or ethyl,
R³ represents H, Cl, methyl, ethyl, n-propyl, tert-butyl, —CH₂OH, —CH₂SH, —CH₂S—CH₃, —CH₂—S—CH₂-furan-2-yl, —CH₂—O—(C=O)—CH₃, —CH₂—S—(C=O)—CH₃—, —CH₂—S—S—CH₃, —CH₂—S—S—CH₂-furan-2-yl or —CH₂—CO₂ethyl,
R⁴ represents H, Br, methyl, —CH₂OH, —CO₂methyl, —CO₂ethyl or —C(=O)CH₃, and
R⁵ represents H or methyl.

Particularly preferred compounds according to the invention are those in which R¹ represents 3,5-dichlorophenyl and R² represents H.

Examples of advantageous compounds of the present invention are selected from the following group:

(5-methylsulfanylmethyl-furan-2-yl)-(5-nitro-pyridin-2-ylamino)-acetic acid (5-bromopyrimidin-2-ylamino)-(5-methylsulfanylmethyl-furan-2-yl)-acetic acid 5-[carboxy-(3,5-dichloropyridin-2-ylamino)-methyl]-2-methyl-furan-3-carboxylic acid ethyl ester 5-[carboxy-(3,5-dibromopyridin-2-ylamino)-methyl]-2-methyl-furan-3-carboxylic acid ethyl ester 5-[carboxy-(3,5-dibromo-6-methyl-pyridin-2-ylamino)-methyl]-2-methyl-furan-3-carboxylic acid ethyl ester (3,5-dibromo-6-methyl-pyridin-2-ylamino)-(4-hydroxymethyl-furan-2-yl)-acetic acid (3,5-dichloro-pyridin-2-ylamino)-(4-methyl-thiophen-2-yl)-acetic acid (2,4-dibromo-5-methyl-phenylamino)-(4-methyl-thiophen-2-yl)-acetic acid (4-methyl-thiophen-2-yl)-(5-nitro-pyridin-2-ylamino)-acetic acid (3,5-dichloro-pyridin-2-ylamino)-furan-2-yl-acetic acid (3,5-dibromopyridin-2-ylamino)-furan-2-yl-acetic acid (3,5-dibromo-6-methyl-pyridin-2-ylamino)-furan-2-yl-acetic acid (3-chloro-5-trifluoromethyl-pyridin-2-ylamino)-furan-2-yl-acetic acid (5-bromopyrimidin-2-ylamino)-furan-2-yl-acetic acid 5-[(3,5-dichloro-phenylamino)-ethoxycarbonyl-methyl]-2-methyl-furan-3-carboxylic acid methyl ester (5-hydroxy-4-phenylazo-1H-pyrazol-3-ylamino)-(5-methylsulfanylmethyl-furan-2-yl)-acetic acid ethyl ester 3-{[ethoxycarbonyl-(4-ethoxycarbonyl-5-methyl-furan-2-yl)-methyl]-amino}-1H-pyrazole-4-carboxylic acid ethyl ester 5-[(4-cyano-5-methylsulfanyl-1H-pyrazol-3-ylamino)-ethoxycarbonyl-methyl]-2-methyl-furan-3-carboxylic acid ethyl ester 5-[(4-cyano-1H-pyrazol-3-ylamino)-ethoxycarbonyl-methyl]-2-methyl-furan-3-carboxylic acid ethyl ester 5-[(4-bromo-2-chloro-phenylamino)-ethoxycarbonyl-methyl]-2-methyl-furan-3-carboxylic acid ethyl ester 5-[(4-cyano-phenylamino)-ethoxycarbonyl-methyl]-2-methyl-furan-3-carboxylic acid ethyl ester (4-hydroxymethyl-furan-2-yl)-(5-hydroxy-4-phenylazo-1H-pyrazol-3-ylamino)-acetic acid ethyl ester (4-cyano-5-methylsulfanyl-1H-pyrazol-3-ylamino)-(4-hydroxymethyl-furan-2-yl)-acetic acid ethyl ester (4-bromo-2-chloro-phenylamino)-(4-hydroxymethyl-furan-2-yl)-acetic acid ethyl ester (3,5-dichloro-phenylamino)-(4-hydroxymethyl-furan-2-yl)-acetic acid ethyl ester (5-chloro-2-methyl-phenylamino)-[5-(furan-2-ylmethylsulfanylmethyl)-furan-2-yl]-acetic acid ethyl ester (2,4-dibromo-phenylamino)-(4-methyl-thiophen-2-yl)-acetic acid (5-chloro-2-methyl-phenylamino)-(5-methylsulfanylmethyl-furan-2-yl)-acetic acid (2-ethyl-phenylamino)-(5-methylsulfanylmethyl-furan-2-yl)-acetic acid (4-sec-butyl-phenylamino)-(5-methylsulfanylmethyl-furan-2-yl)-acetic acid (5-methylsulfanylmethyl-furan-2-yl)-(4-trifluoromethoxy-phenylamino)-acetic acid (2-isopropyl-phenylamino)-(5-methylsulfanylmethyl-furan-2-yl)-acetic acid (2,4-dibromo-phenylamino)-(5-methylsulfanylmethyl-furan-2-yl)-acetic acid (4-tert-butyl-phenylamino)-(5-methylsulfanylmethyl-furan-2-yl)-acetic acid (5-chloro-2-methyl-phenylamino)-[5-(furan-2-ylmethylsulfanylmethyl)-furan-2-yl]-acetic acid (2-ethyl-phenylamino)-[5-(furan-2-ylmethylsulfanylmethyl)-furan-2-yl]-acetic acid (4-sec-butyl-phenylamino)-[5-(furan-2-ylmethylsulfanylmethyl)-furan-2-yl]-acetic acid

[5-(furan-2-ylmethylsulfanylmethyl)-furan-2-yl]-(2-isopropyl-phenylamino)-acetic acid (4-tert-butyl-phenylamino)-[5-(furan-2-ylmethylsulfanylmethyl)-furan-2-yl]-acetic acid 5-[ethoxycarbonyl-(4-iodo-phenylamino)-methyl]-2-methyl-furan-3 carboxylic acid methyl ester 5-[(4-chloro-2-methyl-phenylamino)-ethoxycarbonyl-methyl]-2-methyl-furan-3-carboxylic acid methyl ester 5-[ethoxycarbonyl-(4-phenoxy-phenylamino)-methyl]-2-methyl-furan-3-carboxylic acid methyl ester 5-[ethoxycarbonyl-(4-iodo-phenylamino)-methyl]-2-methyl-furan-3-carboxylic acid ethyl ester 5-[(2-chloro-phenylamino)-ethoxycarbonyl-methyl]-2-methyl-furan-3-carboxylic acid ethyl ester 5-[(4-chloro-2-methyl-phenylamino)-ethoxycarbonyl-methyl]-2-methyl-furan-3-carboxylic acid ethyl ester 5-[(2-chloro-4-fluoro-phenylamino)-ethoxycarbonyl-methyl]-2-methyl-furan-3-carboxylic acid ethyl ester 5-[ethoxycarbonyl-(4-phenoxy-phenylamino)-methyl]-2-methyl-furan-3-carboxylic acid ethyl ester 5-[(2,3-dichloro-phenylamino)-ethoxycarbonyl-methyl]-2-methyl-furan-3-carboxylic acid ethyl ester (4-hydroxymethyl-furan-2-yl)-(4-iodo-phenylamino)-acetic acid ethyl ester (2,4-dichloro-phenylamino)-(4-hydroxymethyl-furan-2-yl)-acetic acid ethyl ester (4-chloro-2-methyl-phenylamino)-(4-hydroxymethyl-furan-2-yl)-acetic acid ethyl ester (4-hydroxymethyl-furan-2-yl)-(4-phenoxy-phenylamino)-acetic acid ethyl ester (2,3-dichloro-phenylamino)-(4-hydroxymethyl-furan-2-yl)-acetic acid ethyl ester (2,3-dichloro-phenylamino)-furan-2-yl-acetic acid ethyl ester 5-[carboxy-(3,5-dibromo-6-methyl-pyridin-2-ylamino)-methyl]-2-methyl-furan-3-carboxylic acid methyl ester (5-methylsulfanylmethyl-furan-2-yl)-(pyrazin-2-ylamino)-acetic acid (3,5-dibromo-pyridin-2-ylamino)-(5-methylsulfanylmethyl-ftiran-2-yl)-acetic acid (3,5-dibromo-6-methyl-pyridin-2-ylamino)-(5-methylsulfanylmethyl-furan-2-yl)-acetic acid 5-[(4-bromo-2-chloro-phenylamino)-carboxy-methyl]-2-methyl-furan-3-carboxylic acid methyl ester 5-[carboxy-(4-cyano-phenylamino)-methyl]-2-methyl-furan-3-carboxylic acid methyl ester 5-[carboxy-(3,5-dichloro-phenylamino)-methyl]-2-methyl-furan-3-carboxylic acid methyl ester 5-[carboxy-(2-phenoxy-phenylamino)-methyl]-2,4-dimethyl-furan-3-carboxylic acid ethyl ester 5-[(4-bromo-2-chloro-phenylamino)-carboxy-methyl]-2,4-dimethyl-furan-3-carboxylic acid ethyl ester 5-[carboxy-(4-cyano-phenylamino)-methyl]-2,4-dimethyl-furan-3-carboxylic acid ethyl ester 5-[carboxy-(3,5-dichloro-phenylamino)-methyl]-2,4-dimethyl-furan-3-carboxylic acid ethyl ester 5-[(4-bromo-2-chloro-phenylamino)-carboxy-methyl]-2-methyl-furan-3-carboxylic acid ethyl ester 5-[carboxy-(4-cyano-phenylamino)-methyl]-2-methyl-furan-3-carboxylic acid ethyl ester 5-[carboxy-(3,5-dichloro-phenylamino)-methyl]-2-methyl-furan-3-carboxylic acid ethyl ester (5-tert-butyl-1H-pyrazol-3-ylamino)-(4-hydroxymethyl-furan-2-yl)-acetic acid (4-bromo-2-chloro-phenylamino)-(3-methyl-thiophen-2-yl)-acetic acid (4-cyano-phenylamino)-(3-methyl-thiophen-2-yl)-acetic acid (3,5-dichloro-phenylamino)-(3-methyl-thiophen-2-yl)-acetic acid (3,5-dichloro-phenylamino)-furan-2-yl-acetic acid

[5-(furan-2-ylmethylsulfanylmethyl)-furan-2-yl]-(4-phenoxy-phenylamino)-acetic acid ethyl ester (5-ethoxycarbonylmethyl-thiophen-2-yl)-(5-hydroxy-4-phenylazo-1H-pyrazol-3-ylamino)-acetic acid ethyl ester {5-1-(4-cyano-1H-pyrazol-3-ylamino)-3-methoxy-2-oxo-propyl]-thiophen-2-yl}-acetic acid ethyl ester (4-ethyl-phenylamino)-(5-methylsulfanylmethyl-furan-2-yl)-acetic acid (3-chloro-2-methyl-phenylamino)-(5-methylsulfanylmethyl-furan-2-yl)-acetic acid (4-chloro-phenylamino)-(5-methylsulfanylmethyl-furan-2-yl)-acetic acid (5-methylsulfanylmethyl-furan-2-yl)-o-tolylamino-acetic acid 5-[carboxy-(4-chloro-3-trifluoromethyl-phenylamino)-methyl]-2-methyl-furan-3-carboxylic acid ethyl ester 5-[carboxy-(2-chloro-phenylamino)-methyl]-2-methyl-furan-3-carboxylic acid ethyl ester 5-[carboxy-(2-chloro-4-fluoro-phenylamino)-methyl]-2-methyl-furan-3-carboxylic acid ethyl ester 5-[carboxy-(4-chloro-2-fluoro-phenylamino)-methyl]-2-methyl-furan-3-carboxylic acid ethyl ester 5-[carboxy-(2,3-dichloro-phenylamino)-methyl]-2-methyl-furan-3-carboxylic acid ethyl ester (2,4-dichloro-phenylamino)-(4-methyl-thiophen-2-yl)-acetic acid (4-chloro-3-trifluoromethyl-phenylamino)-(4-methyl-thiophen-2-yl)-acetic acid (2,4-dichloro-phenylamino)-furan-2-yl-acetic acid (4-chloro-3-trifluoromethyl-phenylamino)-furan-2-yl-acetic acid (4-iodo-phenylamino)-(5-methylsulfanylmethyl-furan-2-yl)-acetic acid (2,4-dichloro-phenylamino)-(5-methylsulfanylmethyl-furan-2-yl)-acetic acid (4-chloro-3-trifluoromethyl-phenylamino)-(5-methylsulfanylmethyl-furan-2-yl)-acetic acid (2-chloro-phenylamino)-(5-methyl sulfanylmethyl-furan-2-yl)-acetic acid (4-chloro-2-methyl-phenylamino)-(5-methylsulfanylhnethyl-furan-2-yl)-acetic acid (2-chloro-4-fluoro-phenylamino)-(5-methylsulfanylmethyl-furan-2-yl)-acetic acid (2-chloro-4-methyl-phenylamino)-(5-methylsulfanylmethyl-furan-2-yl)-acetic acid (2,3-dichloro-phenylamino)-(5-methylsulfanylmethyl-furan-2-yl)-acetic acid

[5-(furan-2-ylmethylsulfanylmethyl)-furan-2-yl]-(4-iodo-phenylamino)-acetic acid (4-chloro-3-trifluoromethyl-phenylamino)-[5-(furan-2-ylmethylsulfanylmethyl)-furan-2-yl]-acetic acid (4-chloro-2-methyl-phenylamino)-[5-(furan-2-ylmethylsulfanylmethyl)-furan-2-yl]-acetic acid (2-chloro-4-methyl-phenylamino)-[5-(furan-2-ylmethylsulfanylmcthyl)-furan-2-yl]-acetic acid (4-chloro-3-trifluoromethyl-phenylamino)-(5-ethoxycarbonylmethyl-thiophen-2-yl)-acetic acid (4-acetyl-3,5-dimethyl-furan-2-yl)-(2-chloro-4-methyl-phenylamino)-acetic acid (4-acetyl-3,5-dimethyl-furan-2-yl)-(2,3-dichloro-phenylamino)-acetic acid (3,5-dichloro-phenylamino)-(5-methylsulfanylmethyl-furan-2-yl)-acetic acid

[2,2']bithiophenyl-5-yl-(3,5-dichloro-phenylamino-acetic acid (3,5-dichloro-phenylamino)-(5-methyldisulfanylmethyl-furan-2-yl)-acetic acid (3-chloro-phenylamino)-(5-mercaptomethyl-furan-2-yl)-acetic acid (3,4-dichloro-phenylamino)-(5-mercaptomethyl-furan-2-yl)-acetic acid (3,5-dichloro-phenylamino)-(5-mercaptomethyl-furan-2-yl)-acetic acid (3,5-dichloro-phenylamino)-(5-methyl-thiophen-2-yl)-acetic acid (3,5-dichloro-phenylamino)-(5-hydroxymethyl-thiophen-2-yl)-acetic acid (5-acetylsulfanylmethyl-furan-2-yl)-(3,5-dichloro-phenylamino)-acetic acid (3,5-dichloro-phenylamino)-(5-ethyl-thiophen-2-yl)-acetic acid (3,5-dichloro-phenylamino)-(5-n-propyl-thiophen-2-yl)-acetic acid (3,5-dichloro-phenylamino)-[5-(furan-2-ylmethylsulfanylmethyl)-furan-2-yl]-acetic acid (3-chloro-phenylamino)-(5-mercaptomethyl-furan-2-yl)-acetic acid (3,4-dichloro-phenylamino)-(5-mercaptomethyl-furan-2-yl)-acetic acid (3,5-dichlorophenylamino)-(thiophen-2-yl)-acetic acid ethyl ester (4-bromofuran-2-yl)-(3,5-dichloro-phenylamino)-acetic acid ethyl ester (3,5-dichloro-phenylamino)-(5-propylthiophen-2-yl)-acetic acid ethyl ester (3,5-dichloro-phenylamino)-(3-methylthiophen-2-yl)-acetic acid ethyl ester (5-tert-butylfuran-2-yl)-(3,5-dichloro-phenylamino)-acetic acid (3,5-dichlorophenylamino)-[5-(fuiran-2-ylmethyldisulfanylmethyl)-furan-2-yl]-acetic acid (3,5-dichlorophenylamino)-(5-methyldisulfanylmethylfuran-2-yl)-acetic acid (3,5-dichlorophenylamino)-[5-(furan-2-ylmethylsulfanylmethyl)-furan-2-yl]-acetic acid 5-acetoxymethylfuran-2-yl-(3,5-dichlorophenylamino)-acetic acid (3,5-dichlorophenylamino)-thiophen-3-yl-acetic acid (3,5-dichlorophenylamino)-(5-methylthiophen-2-yl)-acetic acid (3,5-dichlorophenylamino)-(4-methylthiophen-2-yl)-acetic acid (5-chlorothiophen-2-yl)-(3,5-dichlorophenylamino)-acetic acid and their pharmaceutically acceptable salts.

The compounds according to the invention having the general structure (I)

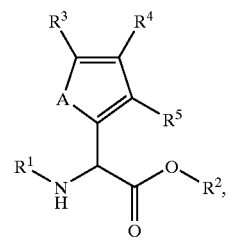

wherein A, $R^1$, $R^2$, $R^3$, $R^4$ and $R^5$ are as defined above, are obtainable according to a process which is also provided by the present invention. According to the inventive process, an amine having the general structure (II)

$$R^1\text{—}NH_2 \qquad \text{II}$$

wherein $R^1$ is as defined above for the general structure (I), is reacted, under the action of an acid, with a glyoxalic acid derivative having the general structure (III)

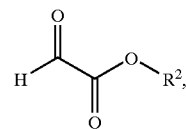

wherein $R^2$ is as defined above for the general structure (I), and with a furan having the general structure (IV-A) or a thiophene having the general structure (IV-B)

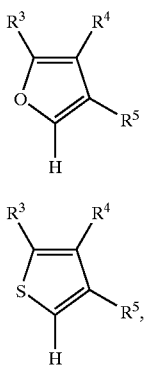

wherein $R^3$, $R^4$ and $R^5$ are as defined above for the general structure (I). If the furan derivative (IV-A) is used, the corresponding amino-furan-2-yl-acetic acid derivative having the general structure (I-A) is obtained as the product, whereas the use of the thiophene derivative (IV-B) yields as the product of the 3-component reaction according to the invention the corresponding amino-thien-2-yl-acetic acid derivative having the general structure (I-B).

For the preparation of the furanylacetic acids (IV-A) and thienylacetic acids (IV-B), that is to say the compounds having the general structure (IV) wherein $R^2$ represents H, the glyoxalic acid reaction component (III) is preferably used in the form of its hydrate.

The process according to the invention can be carried out in the presence of small amounts of an inorganic or, especially, organic acid, for example trifluoroacetic acid, preferably in catalytic amounts of approximately from 1 to 10 mol % (based on the starting material (II)). If there is used as the glyoxalic acid derivative having the general structure (III) glyoxalic acid itself (i.e. the compound (III) wherein $R^2$=H) or its hydrate in a slight excess of approximately from 1.01 to 1.5, preferably from 1.05 to 1.25, molar equivalents (based on the compound (II)), the reaction can be carried out without the addition of an acid or of a further reagent by simply mixing the starting compounds (II), (III) and (IV-A) or (IV-B), preferably in an organic solvent, for example acetonitrile, and then stirring at temperatures of from 0° C. to 100° C.—optionally also as a one-pot process. It is also advantageous to use the furan derivative (IV-A) or thiophene derivative (IV-B) in an excess of, for example, from 1.5 to 4.5 molar equivalents, especially from 2.5 to 3.5 molar equivalents (based on starting material (II)).

In order to achieve maximum conversion of the starting materials to the compounds according to the invention having the general structure (I), a reaction time of from 8 hours to approximately 18 hours, especially 14 hours, is advantageous for the 3-component reaction according to the invention.

Alternatively, it is also possible to carry out the 3-component reaction according to the invention under the action of microwave radiation, whereby the reaction time for largely complete conversion is shortened to a few minutes, for example to from 0.5 minute to 5 minutes. In the case of this procedure, the chosen reaction temperature is preferably from 15° C. to 60° C., especially approximately 50° C. A laboratory microwave from MLS-GmbH (D-88299 Leutkirch, Auenweg 37, Germany), model MLS ETHOS 600 having a power of about 800 W is suitable for the microwave irradiation. The reaction is advantageously carried out, for example, in a pressure-stable Teflon vessel.

The process according to the invention can also be carried out in semi- or fully automated form as the parallel synthesis of a group of compounds according to the invention having the general structure (I). By means of that technique, and by reaction of the compounds (II), (III) and (IV-A) or (IV-B), it is also possible to construct a substance library in the form of an array of compounds. Such a substance library contains the library members, which are the reaction products of the reaction of the compounds (II), (III) and (IV-A) or (IV-B), in the form of individual pure compounds. With the aid of such a substance library, it is possible, for example, to carry out medicinal screening in one or more in vitro screening processes in automated form.

The amines having the general structure (II), the glyoxalic acid derivatives having the general structure (III), the furan derivatives having the general structure (IV-A) and the thiophene derivatives having the general structure (IV-B) used in the process according to the invention are commercially available (from Acros, Geel; Avocado, Port of Heysham; Aldrich, Deisenhofen; Fluka, Seelze; Lancaster, Muilheim; Maybridge, Tintagel; Merck, Darmstadt; Sigma, Deisenhofen; TCI, Japan) or can be prepared by processes generally known in the art.

The compounds according to the invention having the general structure (I) can be isolated both in the depicted form and in the form of a salt. The compound according to the invention having the general structure (I) is usually obtained after the reaction according to the above-described process has taken place and after subsequent conventional working up. The compound having the general structure (I) so obtained or formed in situ without isolation can then be converted into the corresponding salt, for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. If the compounds according to the invention of the general formula (I) are acids, especially carboxylic acids, the salt formation can be effected by addition of a physiologically tolerable base, for example $NaHCO_3$ or sodium carbonate; the formation of the sodium salt in particular is preferred for the carboxylic acids. The salts that are formed are, inter alia, hydrochlorides, hydrobromides, phosphates, carbonates, hydrogen carbonates, formates, acetates, oxalates, succinates, tartrates, fumarates, citrates and glutamates. Formation of the hydrochloride, which is particularly preferred, can also be effected by addition of trimethylsilyl chloride (TMSCl) to the base dissolved in a suitable organic solvent, such as butan-2-one (methyl ethyl ketone), advantageously in the presence of water.

If the compounds having the general structure (I) are obtained in the preparation process according to the invention in the form of racemates or in the form of mixtures of their different enantiomers and/or diastereoisomers, such mixtures can be separated by processes which are well known in the art. Suitable methods are, inter alia, chromatographic separation processes, especially liquid chromatography processes under normal or elevated pressure, preferably MPLC and HPLC processes, and also fractional crystallization processes. By means of such processes it is possible especially to separate from one another, for example by means of HPLC on chiral phase or by means of crystallization, individual enantiomers of diastereoisomeric salts formed with chiral acids, for example (+)-tartaric acid, (−)-tartaric acid or (+)-10-camphorsulfonic acid, or—where acids are concerned—with chiral bases, for example brucine or (−)-ephedrine.

The present invention also provides a medicament containing at least one compound having the general structure (I) as defined above or a pharmaceutical salt thereof, especially the hydrochloride salt. The medicament according to the invention preferably contains at least one of the compounds mentioned by way of example above in substance or in the form of a pharmaceutically acceptable salt, and optionally further active ingredients and excipients.

Such medicaments according to the invention are preferably used in the therapy of pain, for example, acute pain, chronic pain or neuropathic pain. It has also been found that the medicaments according to the invention can also successfully be used in the treatment of migraine, inflammatory and/or allergic reactions, depression, drug and/or alcohol abuse, gastritis, diarrhoea, urinary incontinence, cardiovascular diseases, respiratory diseases, coughs, mental diseases, neurodegenerative diseases, epilepsy, schizophrenia, Alzheimer's disease, Huntington's disease, Parkinson's disease, cerebral ischaemia, cerebral infarct, psychoses caused by increased amino acid levels, strokes, cerebral oedemas, deficiencies of the central nervous system, hypoxia, anoxia, AIDS dementia, encephalomyelitis, Tourette syndrome, perinatal asphyxia, or for anxiolysis.

The present Application relates also to the use of at least one substituted amino-furan-2-yl-acetic acid derivative of formula (I-A) or substituted amino-thien-2-yl-acetic acid derivative of formula (I-B) in the preparation of a medicament for the treatment of pain, migraine, inflammatory and/or allergic reactions, depression, drug and/or alcohol abuse, gastritis, diarrhoea, urinary incontinence, cardiovascular diseases, respiratory diseases, coughs, mental diseases, neurodegenerative diseases, epilepsy, schizophrenia, Alzheimer's disease, Huntington's disease, Parkinson's disease, cerebral ischaemia, cerebral infarct, psychoses caused by increased amino acid levels, strokes, cerebral oedemas, deficiencies of the central nervous system, hypoxia, anoxia, AIDS dementia, encephalomyelitis, Tourette syndrome, perinatal asphyxia, or for anxiolysis.

The present invention also provides pharmaceutical compositions that contain at least one compound having the general structure (I) as defined above, or a pharmaceutically acceptable salt thereof, as well as one or more pharmaceutical excipients.

The medicaments and pharmaceutical compositions according to the invention can be in liquid, semi-solid or solid pharmaceutical dosage forms and can be administered in the form of, for example, injectable solutions, drops, juices, syrups, sprays, suspensions, granules, tablets, pellets, transdermal therapeutic systems, capsules, plasters, suppositories, ointments, creams, lotions, gels, emulsions or aerosols, and, in addition to at least one compound according to the invention having the general structure (I), they contain, according to the particular formation and depending on the route of administration, pharmaceutical excipients, such as carriers, fillers, solvents, diluents, surface-active substances, colorings, preservatives, disintegrators, glidants, lubricants, flavorings and/or binders. Such excipients may be, for example: water, ethanol, 2-propanol, glycerol, ethylene glycol, propylene glycol, polyethylene glycol, polypropylene glycol, glucose, fructose, lactose, saccharose, dextrose, molasses, starch, modified starch, gelatin, sorbitol, inositol, mannitol, microcrystalline cellulose, methyl cellulose, carboxymethyl cellulose, cellulose acetate, shellac, cetyl alcohol, polyvinylpyrrolidone, paraffins, waxes, natural and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soybean oil, lecithin, sodium lactate, polyoxyethylene and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potassium carbonate, calcium phosphate, dicalcium phosphate, potassium bromide, potassium iodide, talcum, kaolin, pectin, crospovidone, agar and bentonite.

The choice of excipients and the amounts thereof to be used depend on whether the medicament is to be administered by the oral, subcutaneous, parenteral, intravenous, vaginal, pulmonary, intraperitoneal, transdermal, intramuscular, nasal, buccal or rectal route, or locally, for example to infections of the skin, the mucosa and of the eyes. For oral administration there are suitable, inter alia, preparations in the form of tablets, dragées, capsules, granules, drops, juices and syrups, and for parenteral and topical administration and for administration by inhalation there are suitable solutions, suspensions, readily reconstitutable powders for inhalation, and also sprays. Compounds according to the invention having the general structure I in a depot formulation in dissolved form or in a plaster, optionally with the addition of agents promoting penetration of the skin, are suitable preparations for percutaneous administration. Forms of preparation for rectal, transmucosal, parenteral, oral or percutaneous administration may release the compounds according to the invention having the general structure (I) in a delayed manner.

The medicaments and pharmaceutical compositions according to the invention are prepared by means, devices, methods and processes which are well known in the art of pharmaceutical formulation, as are described, for example, in "Remington's Pharmaceutical Sciences," ed. A. R. Gennaro, 17th ed., Mack Publishing Company, Easton, Pa. (1985), especially in Part 8, Chapter 76 to 93.

Accordingly, for a solid formulation, for example, a tablet, the active ingredient of the medicament, i.e. a compound having the general structure (I) or a pharmaceutically acceptable salt thereof, can be granulated with a pharmaceutical carrier, for example conventional tablet constituents such as maize starch, lactose, saccharose, sorbitol, talcum, magnesium stearate, dicalcium phosphate or pharmaceutically acceptable gums, and pharmaceutical diluents, for example, water, in order to form a solid composition which contains a compound according to the invention or a pharmaceutically acceptable salt thereof in homogeneous distribution. Homogeneous distribution is here understood to mean that the active ingredient is distributed evenly throughout the entire composition, so that the latter can readily be divided into unit dose forms, such as tablets, pills or capsules, which each have the same effectiveness. The solid composition is then divided into unit dose forms. It is also possible for the tablets or pills of the medicament according to the invention or of the compositions according to the invention to be coated or otherwise compounded, in order to prepare a delayed-release dosage form. Suitable coating agents are, inter alia, polymeric acids and mixtures of polymeric acids with materials such as, for example, shellac, cetyl alcohol and/or cellulose acetate.

The amount of active ingredient to be administered to a patient varies and is dependent on the weight, the age and the history of past disease in the patient, and also on the mode of administration, the indication and the severity of the disease. Normally, from 0.1 to 5000 mg/kg, especially from 1 to 500 mg/kg, preferably from 2 to 250 mg/kg body weight of at least one compound according to the invention having the general structure (I) are administered.

The present invention is explained further hereinbelow by means of Examples, without limiting it thereto.

EXAMPLES

Preliminary Remarks

The chemicals and solvents used were purchased from Acros, Geel; Avocado, Port of Heysham; Aldrich, Deisenhofen; Fluke, Seelze; Lancaster, Muilheim; Maybridge, Tintagel; Merck, Darmstadt; Sigma, Deisenhofen and TCI, Japan or were synthesized by conventional processes generally known to those skilled in the art.

Thin-layer chromatographic investigations were carried out using HPTLC precoated plates, silica gel 60 F 254, from E. Merck, Darmstadt, Germany.

ESI mass spectra were recorded using a LCQ Classic mass spectrometer from Finnigan, and $^1$H-NMR spectra were recorded with a 300 MHz Avance DPX 300 NMR device or a 600 MHz Avance DRX 600 NMR device from Bruker.

Example 1-General Working Procedure 1 (GWP 1)

A round-bottomed glass test tube (diameter 16 mm, length 125 mm) with a thread was provided with a magnetic stirring core and closed in an automated manner with a screw lid having a septum. By means of a robot, the test tube was placed in a stirring block adjusted to a temperature of 20° C. The following reagents were pipetted in in succession by a robot:

1 ml of a solution containing trifluoroacetic acid and the amine component (II)—in each case 0.1M—in acetonitrile 1 ml of a 0.11 M glyoxalic acid derivative (III) solution in acetonitrile 1 ml of a 0.3 M furan (IV-A) or thiophene (IV-B) solution in acetonitrile.

The reaction mixture was stirred for 600 minutes at 40° C. in a stirring block. The reaction solution was then filtered off. The test tube was rinsed twice with 1.5 ml of a 7.5% NaHCO$_3$ solution.

The rack with the samples was then placed manually onto a working-up unit. 2 ml of ethyl acetate were added to the reaction mixture in a vortexer, and shaking was carried out. To form the phase boundary, centrifugation was carried out for a short time in a centrifuge. The phase boundary was detected visually and the organic phase was removed by means of a pipette. In the next step, a further 2 ml of ethyl acetate was added to the aqueous phase, followed by shaking, centrifugation and removal of the organic phase by means of a pipette. The combined organic phases are dried over 2.4 g of MgSO$_4$ (granulated). The solvent was removed in a vacuum centrifuge. Each sample was analyzed by ESI-MS and/or NMR.

The automatic synthesis ensured that all samples were treated equally and that the reaction procedure was highly constant.

The synthesized and isolated compounds are shown in Table 1.

TABLE 1

| Example No. | Compound | Molar mass calculated | Molar mass found |
|---|---|---|---|
| 1 | (5-Methylsulfanylmethyl-furan-2-yl)-(5-nitro-pyridin-2-ylamino)-acetic acid | 323.32 | 323.9; 278.1 (M-CO$_2$) |
| 2 | (5-Bromopyrimidin-2-ylamino)-(5-methylsulfanyl-methyl-furan-2-yl)-acetic acid | 358.21 | 356.9/359.0 |
| 3 | 5-[Carboxy-(3,5-dichloropyridin-2-ylamino)-methyl]-2-methyl-furan-3-carboxylic acid ethyl ester | 373.19 | 372.9/374.9 |
| 4 | 5-[Carboxy-(3,5-dibromopyridin-2-ylamino)-methyl]-2-methyl-furan-3-carboxylic acid ethyl ester | 462.1 | 460.7/462.8/464.8 |
| 5 | 5-[Carboxy-(3,5-dibromo-6-methyl-pyridin-2-ylamino)-methyl]-2-methyl-furan-3-carboxylic acid ethyl ester | 476.13 | 474.9/476.9/478.8 |
| 6 | (3,5-Dibromo-6-methyl-pyridin-2-ylamino)-(4-hydroxymethyl-furan-2-yl)-acetic acid | 420.06 | 420.9/422.9 |
| 7 | (3,5-Dichloro-pyridin-2-ylamino)-(4-methyl-thiophen-2-yl)-acetic acid | 317.19 | 316.9/318.9 |
| 8 | (2,4-Dibromo-5-methyl-phenylamino)-(4-methyl-thiophen-2-yl)-acetic acid | 419.14 | 420.8/422.8 |
| 9 | (4-Methyl-thiophen-2-yl)-(5-nitro-pyridin-2-ylamino)-acetic acid | 293.3 | 293.9; 248.2 (M-CO$_2$) |
| 10 | (3,5-Dichloro-pyridin-2-ylamino)-furan-2-yl-acetic acid | 287.1 | 286.9/289.0 |
| 11 | (3,5-Dibromopyridin-2-ylamino)-furan-2-yl-acetic acid | 376.01 | 376.9/378.9 |
| 12 | (3,5-Dibromo-6-methyl-pyridin-2-ylamino)-furan-2-yl-acetic acid | 390.04 | 390.9/392.9 |
| 13 | (3-Chloro-5-trifluoromethyl-pyridin-2-ylamino)-furan-2-yl-acetic acid | 320.65 | 320.9/322.9 |
| 14 | (5-Bromopyrimidin-2-ylamino)-furan-2-yl-acetic acid | 298.1 | 297.0/299.0 |
| 15 | 5-[(3,5-Dichloro-phenylamino)-ethoxycarbonyl-methyl]-2-methyl-furan-3-carboxylic acid methyl ester | 386.23 | 385.9/387.9 |
| 16 | (5-Hydroxy-4-phenylazo-1H-pyrazol-3-ylamino)-(5-methylsulfanylmethyl-furan-2-yl)-acetic acid ethyl ester | 415.47 | 416.0 |
| 17 | 3-{[Ethoxycarbonyl-(4-ethoxycarbonyl-5-methyl-furan-2-yl)-methyl]-amino}-1H-pyrazole-4-carboxylic acid ethyl ester | 393.39 | 393.9 |

TABLE 1-continued

| Example No. | Compound | Molar mass calculated | Molar mass found |
|---|---|---|---|
| 18 | 5-[(4-Cyano-5-methylsulfanyl-1H-pyrazol-3-ylamino)-ethoxycarbonyl-methyl]-2-methyl-furan-3-carboxylic acid ethyl ester | 392.43 | 392.9 |
| 19 | 5-[(4-Cyano-1H-pyrazol-3-ylamino)-ethoxycarbonyl-methyl]-2-methyl-furan-3-carboxylic acid ethyl ester | 346.34 | 346.9 |
| 20 | 5-[(4-Bromo-2-chloro-phenylamino)-ethoxycarbonyl-methyl]-2-methyl-furan-3-carboxylic acid ethyl ester | 444.71 | 443.9/445.9 |
| 21 | 5-[(4-Cyano-phenylamino)-ethoxycarbonyl-methyl]-2-methyl-furan-3-carboxylic acid ethyl ester | 356.37 | 357.0 |
| 22 | (4-Hydroxymethyl-furan-2-yl)-(5-hydroxy-4-phenylazo-1H-pyrazol-3-ylamino)-acetic acid ethyl ester | 385.37 | 386.0 |
| 23 | (4-Cyano-5-methylsulfanyl-1H-pyrazol-3-ylamino)-(4-hydroxymethyl-furan-2-yl)-acetic acid ethyl ester | 336.36 | 336.9 |
| 24 | (4-Bromo-2-chloro-phenylamino)-(4-hydroxymethyl-furan-2-yl)-acetic acid ethyl ester | 388.64 | 387.9/389.9 |
| 25 | (3,5-Dichloro-phenylamino)-(4-hydroxymethyl-furan-2-yl)-acetic acid ethyl ester | 344.19 | 344.0/346.0 |
| 26 | (5-Chloro-2-methyl-phenylamino)-[5-(furan-2-ylmethylsulfanylmethyl)-furan-2-yl]-acetic acid ethyl ester | 419.92 | 420.0 |
| 27 | (2,4-Dibromo-phenylamino)-(4-methyl-thiophen-2-yl)-acetic acid | 405.11 | ($M-CO_2$) 358.2/360.2/362.2 |
| 28 | (5-Chloro-2-methyl-phenylamino)-(5-methylsulfanyl-methyl-furan-2-yl)-acetic acid | 325.81 | 326.0 |
| 29 | (2-Ethyl-phenylamino)-(5-methylsulfanylmethyl-furan-2-yl)-acetic acid | 305.39 | 306.0 |
| 30 | (4-sec-Butyl-phenylamino)-(5-methylsulfanylmethyl-furan-2-yl)-acetic acid | 333.44 | 334.1 |
| 31 | (5-Methylsulfanylmethyl-furan-2-yl)-(4-trifluoro-methoxy-phenylamino)-acetic acid | 361.33 | 362.0/ 316.2 ($M-CO_2$) |
| 32 | (2-Isopropyl-phenylamino)-(5-methylsulfanylmethyl-furan-2-yl)-acetic acid | 319.42 | 320.1 |
| 33 | (2,4-Dibromo-phenylamino)-(5-methylsulfanylmethyl-furan-2-yl)-acetic acid | 435.14 | ($M-CO_2$) 390.0/392.0 |
| 34 | (4-tert-Butyl-phenylamino)-(5-methylsulfanylmethyl-furan-2-yl)-acetic acid | 333.44 | 334.0 |
| 35 | (5-Chloro-2-methyl-phenylamino)-[5-(furan-2-ylmethylsulfanylmethyl)-furan-2-yl]-acetic acid | 391.87 | 392.0/394.0 |
| 36 | (2-Ethyl-phenylamino)-[5-(furan-2-ylmethylsulfanyl-methyl)-furan-2-yl]-acetic acid | 371.45 | 372.1 |
| 37 | (4-sec-Butyl-phenylamino)-[5-(furan-2-ylmethyl-sulfanylmethyl)-furan-2-yl]-acetic acid | 399.5 | 400.1 |
| 38 | [5-(Furan-2-ylmethylsulfanylmethyl)-furan-2-yl]-(2-isopropyl-phenylamino)-acetic acid | 385.48 | 386.2 |
| 39 | (4-tert-Butyl-phenylamino)-[5-(furan-2-ylmethyl-sulfanylmethyl)-furan-2-yl]-acetic acid | 399.5 | 400.1 |
| 40 | 5-[Ethoxycarbonyl-(4-iodo-phenylamino)-methyl]-2-methyl-furan-3-carboxylic acid methyl ester | 443.23 | 442.1/444.0/445.0 |
| 41 | 5-[(4-Chloro-2-methyl-phenylamino)-ethoxycarbonyl-methyl]-2-methyl-furan-3-carboxylic acid methyl ester | 365.81 | 366.1/368.1 |
| 42 | 5-[Ethoxycarbonyl-(4-phenoxy-phenylamino)-methyl]-2-methyl-furan-3-carboxylic acid methyl ester | 409.43 | 408.3/410.2 |
| 43 | 5-[Ethoxycarbonyl-(4-iodo-phenylamino)-methyl]-2-methyl-furan-3-carboxylic acid ethyl ester | 457.26 | 456.2/458.0/459.1 |
| 44 | 5-[(2-Chloro-phenylamino)-ethoxycarbonyl-methyl]-2-methyl-furan-3-carboxylic acid ethyl ester | 365.81 | 366.1/367.0/368.1 |
| 45 | 5-[(4-Chloro-2-methyl-phenylamino)-ethoxycarbonyl-methyl]-2-methyl-furan-3-carboxylic acid ethyl ester | 379.83 | 380.1/382.1 |
| 46 | 5-[(2-Chloro-4-fluoro-phenylamino)-ethoxycarbonyl-methyl]-2-methyl-furan-3-carboxylic acid ethyl ester | 383.8 | 384.1/385.0 |
| 47 | 5-[Ethoxycarbonyl-(4-phenoxy-phenylamino)-methyl]-2-methyl-furan-3-carboxylic acid ethyl ester | 423.46 | 422.4/424.2 |
| 48 | 5-[(2,3-Dichloro-phenylamino)-ethoxycarbonyl-methyl]-2-methyl-furan-3-carboxylic acid ethyl ester | 400.25 | 400.0/402.0 |
| 49 | (4-Hydroxymethyl-furan-2-yl)-(4-iodo-phenylamino)-acetic acid ethyl ester | 401.19 | 402.2 |
| 50 | (2,4-Dichloro-phenylamino)-(4-hydroxymethyl-furan-2-yl)-acetic acid ethyl ester | 344.19 | 344.2/346.2 |
| 51 | (4-Chloro-2-methyl-phenylamino)-(4-hydroxymethyl-furan-2-yl)-acetic acid ethyl ester | 323.77 | 324.3 |
| 52 | (4-Hydroxymethyl-furan-2-yl)-(4-phenoxy-phenyl-amino)-acetic acid ethyl ester | 367.4 | 368.3 |
| 53 | (2,3-Dichloro-phenylamino)-(4-hydroxymethyl-furan-2-yl)-acetic acid ethyl ester | 344.19 | 344.1/346.1 |

TABLE 1-continued

| Example No. | Compound | Molar mass calculated | Molar mass found |
|---|---|---|---|
| 54 | (2,3-Dichloro-phenylamino)-furan-2-yl-acetic acid ethyl ester | 314.16 | 314.4/316.3 |
| 55 | 5-[Carboxy-(3,5-dibromo-6-methyl-pyridin-2-ylamino)-methyl]-2-methyl-furan-3-carboxylic acid methyl ester | 462.1 | 460.9/462.9/464.9 |
| 56 | (5-Methylsulfanylmethyl-furan-2-yl)-(pyrazin-2-ylamino)-acetic acid | 279.31 | 280.0 |
| 57 | (3,5-Dibromo-pyridin-2-ylamino)-(5-methylsulfanyl-methyl-furan-2-yl)-acetic acid | 436.13 | 436.8/438.8 |
| 58 | (3,5-Dibromo-6-methyl-pyridin-2-ylamino)-(5-methyl-sulfanylmethyl-furan-2-yl)-acetic acid | 450.15 | 448.9/450.8/452.8 |
| 59 | 5-[(4-Bromo-2-chloro-phenylamino)-carboxy-methyl]-2-methyl-furan-3-carboxylic acid methyl ester | 402.63 | (M-$CO_2$) 356.4/358.4/360.3 |
| 60 | 5-[Carboxy-(4-cyano-phenylamino)-methyl]-2-methyl-furan-3-carboxylic acid methyl ester | 314.29 | (M-$CO_2$) 269.4 |
| 61 | 5-[Carboxy-(3,5-dichloro-phenylamino)-methyl]-2-methyl-furan-3-carboxylic acid methyl ester | 358.17 | 358.0/360.0 (M-$CO_2$) 312.4 |
| 62 | 5-[Carboxy-(2-phenoxy-phenylamino)-methyl]-2,4-dimethyl-furan-3-carboxylic acid ethyl ester | 409.43 | 410.1 (M-$CO_2$) 364.4 |
| 63 | 5-[(4-Bromo-2-chloro-phenylamino)-carboxy-methyl]-2,4-dimethyl-furan-3-carboxylic acid ethyl ester | 430.68 | (M-$CO_2$) 384.3/386.2/388.2 |
| 64 | 5-[Carboxy-(4-cyano-phenylamino)-methyl]-2,4-dimethyl-furan-3-carboxylic acid ethyl ester | 342.35 | (M-$CO_2$) 297.4 |
| 65 | 5-[Carboxy-(3,5-dichloro-phenylamino)-methyl]-2,4-dimethyl-furan-3-carboxylic acid ethyl ester | 386.23 | (M-$CO_2$) 340.3/342.3 |
| 66 | 5-[(4-Bromo-2-chloro-phenylamino)-carboxy-methyl]-2-methyl-furan-3-carboxylic acid ethyl ester | 416.65 | 418.0, (M-$CO_2$) 370.4/372.3 |
| 67 | 5-[Carboxy-(4-cyano-phenylamino)-methyl]-2-methyl-furan-3-carboxylic acid ethyl ester | 328.32 | (M-$CO_2$) 283.4 |
| 68 | 5-[Carboxy-(3 5-dichloro-phenylamino)-methyl]-2-methyl-furan-3-carboxylic acid ethyl ester | 372.2 | 372.0/374.0 (M-$CO_2$) 326.3 |
| 69 | (5-tert-Butyl-1H-pyrazol-3-ylamino)-(4-hydroxy-methyl-furan-2-yl)-acetic acid | 293.32 | 294.5 |
| 70 | (4-Bromo-2-chloro-phenylamino)-(3-methyl-thiophen-2-yl)-acetic acid | 360.66 | (M-$CO_2$) 314.4/316.3/318.3 |
| 71 | (4-Cyano-phenylamino)-(3-methyl-thiophen-2-yl)-acetic acid | 272.32 | (M-$CO_2$) 227.4 |
| 72 | (3,5-Dichloro-phenylamino)-(3-methyl-thiophen-2-yl)-acetic acid | 316.2 | (M-$CO_2$) 270.4/272.4 |
| 73 | (3,5-Dichloro-phenylamino)-furan-2-yl-acetic acid | 286.11 | 286.3/288.3 (M-$CO_2$) 240.6/242.5 |
| 74 | [5-(Furan-2-ylmethylsulfanylmethyl)-furan-2-yl]-(4-phenoxy-phenylamino)-acetic acid ethyl ester | 463.55 | 464.0 |
| 75 | (5-Ethoxycarbonylmethyl-thiophen-2-yl)-(5-hydroxy-4-phenylazo-1H-pyrazol-3-ylamino)-acetic acid ethyl ester | 457.5 | 458.0 |
| 76 | {5-[1-(4-Cyano-1H-pyrazol-3-ylamino)-3-methoxy-2-oxo-propyl]-thiophen-2-yl}-acetic acid ethyl ester | 362.4 | 363.0 |
| 77 | (4-Ethyl-phenylamino)-(5-methylsulfanylmethyl-furan-2-yl)-acetic acid | 305.39 | 306.1, (M-$CO_2$) 260.2 |
| 78 | (3-Chloro-2-methyl-phenylamino)-(5-methylsulfanyl-methyl-furan-2-yl)-acetic acid | 325.81 | 326.0/328.0, (M-$CO_2$) 280.2 |
| 79 | (4-Chloro-phenylamino)-(5-methylsulfanylmethyl-furan-2-yl)-acetic acid | 311.78 | 311.9/314.0, (M-$CO_2$) 266.1 |
| 80 | (5-Methylsulfanylmethyl-furan-2-yl)-o-tolylamino-acetic acid | 291.36 | 292.1, (M-$CO_2$) 246.2 |
| 81 | 5-[Carboxy-(4-chloro-3-trifluoromethyl-phenylamino)-methyl]-2-methyl-furan-3-carboxylic acid ethyl ester | 405.75 | (M-$CO_2$) 360.0/362.1 |
| 82 | 5-[Carboxy-(2-chloro-phenylamino)-methyl]-2-methyl-furan-3-carboxylic acid ethyl ester | 337.75 | 338.0, (M-$CO_2$) 292.2 |
| 83 | 5-[Carboxy-(2-chloro-4-fluoro-phenylamino)-methyl]-2-methyl-furan-3-carboxylic acid ethyl ester | 355.74 | 356.8/358.9, (M-$CO_2$) 310.2/312.2 |
| 84 | 5-[Carboxy-(4-chloro-2-fluoro-phenylamino)-methyl]-2-methyl-furan-3-carboxylic acid ethyl ester | 355.74 | (M-$CO_2$) 310.2/312.2 |
| 85 | 5-[Carboxy-(2,3-dichloro-phenylamino)-methyl]-2-methyl-furan-3-carboxylic acid ethyl ester | 372.2 | (M-$CO_2$) 310.2/312.2 |
| 86 | (2,4-Dichloro-phenylamino)-(4-methyl-thiophen-2-yl)-acetic acid | 316.2 | (M-$CO_2$) 270.3/272.3 |
| 87 | (4-Chloro-3-trifluoromethyl-phenylamino)-(4-methyl-thiophen-2-yl)-acetic acid | 349.75 | (M-$CO_2$) 304.4/306.3 |

TABLE 1-continued

| Example No. | Compound | Molar mass calculated | Molar mass found |
|---|---|---|---|
| 88 | (2,4-Dichloro-phenylamino)-furan-2-yl-acetic acid | 286.11 | 286.3/288.1, (M-$CO_2$) 240.4/242.4 |
| 89 | (4-Chloro-3-trifluoromethyl-phenylamino)-furan-2-yl-acetic acid | 319.66 | (M-$CO_2$) 274.5/276.5 |
| 90 | (4-Iodo-phenylamino)-(5-methylsulfanylmethyl-furan-2-yl)-acetic acid | 403.23 | 403.9, (M-$CO_2$) 358.1 |
| 91 | (2,4-Dichloro-phenylamino)-(5-methylsulfanylmethyl-furan-2-yl)-acetic acid | 346.23 | (M-$CO_2$) 300.2/302.1 |
| 92 | (4-Chloro-3-trifluoromethyl-phenylamino)-(5-methyl-sulfanylmethyl-furan-2-yl)-acetic acid | 379.78 | (M-$CO_2$) 334.1/336.1 |
| 93 | (2-Chloro-phenylamino)-(5-methylsulfanylmethyl-furan-2-yl)-acetic acid | 311.78 | 312.0/314.0, (M-$CO_2$) 366.2/368.2 |
| 94 | (4-Chloro-2-methyl-phenylamino)-(5-methylsulfanyl-methyl-furan-2-yl)-acetic acid | 325.81 | 326.0/328.0, (M-$CO_2$) 280.2/282.2 |
| 95 | (2-Chloro-4-fluoro-phenylamino)-(5-methylsulfanyl-methyl-furan-2-yl)-acetic acid | 329.77 | 330.0, (M-$CO_2$) 284.2/286.2 |
| 96 | (2-Chloro-4-methyl-phenylamino)-(5-methylsulfanyl-methyl-furan-2-yl)-acetic acid | 325.81 | 326.0/328.0, (M-$CO_2$) 280.2 |
| 97 | (2,3-Dichloro-phenylamino)-(5-methylsulfanylmethyl-furan-2-yl)-acetic acid | 346.23 | (M-$CO_2$) 300.2/302.1 |
| 98 | [5-(Furan-2-ylmethylsulfanylmethyl)-furan-2-yl]-(4-iodo-phenylamino)-acetic acid | 469.29 | 470.1/471.7 |
| 99 | (4-Chloro-3-trifluoromethyl-phenylamino)-[5-(furan-2-ylmethylsulfanylmethyl)-furan-2-yl]-acetic acid | 445.84 | 446.7/447.6 (M-$CO_2$) 400.6/401.5 |
| 100 | (4-Chloro-2-methyl-phenylamino)-[5-(furan-2-ylmethylsulfanylmethyl)-furan-2-yl]-acetic acid | 391.87 | 392.5/393.4 |
| 101 | (2-Chloro-4-methyl-phenylamino)-[5-(furan-2-ylmethylsulfanylmethyl)-furan-2-yl]-acetic acid | 391.87 | 392.2/394.8 |
| 102 | (4-Chloro-3-trifluoromethyl-phenylamino)-(5-ethoxy-carbonylmethyl-thiophen-2-yl)-acetic acid | 421.82 | (M-$CO_2$) 376.4/378.4 |
| 103 | (4-Acetyl-3,5-dimethyl-furan-2-yl)-(2-chloro-4-methyl-phenylamino)-acetic acid | 335.78 | (M-$CO_2$) 290.3/292.2 |
| 104 | (4-Acetyl-3,5-dimethyl-furan-2-yl)-(2,3-dichloro-phenylamino)-acetic acid | 356.2 | (M-$CO_2$) 310.3/312.2 |
| 106 | (3,5-Dichloro-phenylamino)-(5-methylsulfanylmethyl-furan-2-yl)-acetic acid | 346.23 | 345.9/347.9; 300.0/302.0 (M-$CO_2$) |
| 113 | (3-Chloro-phenylamino)-(5-mercaptomethyl-furan-2-yl)-acetic acid | 297.8 | 297.9 (MH) |
| 114 | (3,4-Dichloro-phenylamino)-(5-mercaptomethyl-furan-2-yl)-acetic acid | 332.2 | 332.0 (MH) |

Example 2-General Working Procedure 2 (GWP 2)

3,5-Dichloroaniline (10 mmol), glyoxalic acid hydrate (11 mmol) and the furan derivative (IV-A) or thiophene derivative (IV-B) (30 mmol) were dissolved in 10 ml of acetonitrile and stirred for 14 hours at 40° C. The reaction mixture was concentrated and purified by means of RP4 silica gel MPLC (Polygoprep 60-130 C4, Macherey-Nagel, P.O. Box 101352, D-52313 Duiren, Germany) using methanol/water mixtures of various compositions and with the addition of 0.1% glacial acetic acid. After concentration of the product fractions using a rotary evaporator, the product was isolated in the form of an oil.

General Working Procedure 3 (GWP 3)—Microwave Irradiation

The reactions with microwave irradiation were carried out in a laboratory microwave of type MLS ETHOS 600 from MLS-GmbH (D-88299 Leutkirch, Auenweg 37, Germany).

For the synthesis, the reaction components (II), (III) and (IV-A) or (IV-B) and the solvent were placed in a pressure-stable Teflon vessel which was closed with a Teflon lid and clamped into a safety holder for letting off excess pressure. Control of the reaction temperature took place in a second Teflon vessel which contained the same solvent as used in the synthesis. Temperature control was carried out by way of an internal glass fibre optics, which was guided in a quartz tube and was controlled from the outside by a control computer.

3,5-Dichloroaniline (10 mmol), glyoxalic acid hydrate (11 mmol) and furan derivative (IV-A) or thiophene derivative (IV-B) (30 mmol) were dissolved in 10 ml of acetonitrile, heated to 50° C. in the course of one minute in the microwave and left at that temperature for five minutes. The microwave radiation was radiated with a power of 800 Watts, which was controlled and regulated by a control computer. After cooling, the vessel was placed in ice-water and opened carefuilly, and the solvent was removed using a rotary evaporator.

Purification was carried out by means of RP4 silica gel MPLC (Polygoprep 60-130 C4, Macherey-Nagel, P.O. Box 101352, D-52313 Duren, Germany) using methanol/water mixtures of various compositions and with the addition of 0.1% glacial acetic acid. After concentration of the product fractions using a rotary evaporator, the product was isolated in the form of an oil.

In order to prepare the hydrochloride salt, the crude product was dissolved in butan-2-one, and an equimolar amount of water and then an equimolar amount of TMSCl were added thereto, while cooling with ice and with stirring. After standing overnight, the precipitated HCl salt was filtered off with suction and dried, or precipitation was brought about by removal of the solvent in vacuo.

The $^1$H-NMR data of some of the compounds prepared according to GWP 2 and 3 are shown hereinbelow; the NMR data were obtained at 600 MHz, with $d_6$-DMSO being used as solvent:

(3,5-Dichloro-phenylamino)-(thiophen-2-yl)-acetic Acid Ethyl Ester (115)

δ=1.20 ppm (t, 3H, CH$_3$); 4.16 ppm (q, 2H, OCH$_2$); 5.65 ppm (d, 1H, α-CH); 6.65 ppm (s, 1H, aryl-4-H); 6.80 ppm (s, 2H, aryl-2-H and aryl-6-H); 7.10 ppm (m, 1H, thiophene-H); 7.20 ppm (d, 1H, thiophene-H); 7.50 ppm (d, 1H, thiophene-H).

(4-Bromofuran-2-yl)-(3,5-dichlorophenylamino)-acetic Acid Ethyl Ester (116)

δ=1.15ppm (t, 3H, CH$_3$); 4.15 ppm (q, 2H, OCH$_2$); 5.50 ppm (d, 1H, α-CH); 6.60 ppm (s, 1H, furan-H); 6.70 ppm (s, 1H, furan-H); 6.75 ppm (s, 1H, aryl-4-H); 6.80 ppm (s, 2H, aryl-2-H and aryl-6H); 7.80 ppm (d, 1H, α-NH).

(3,5-Dichlorophenylamino)-(5-propylthiophen-2-yl)-acetic Acid Ethyl Ester Hydrochloride (117-HCl)

δ=0.95 ppm (t, 3H, CH$_3$); 1.20 ppm (t, 3H, CH$_3$); 1.60 ppm (q, 2H, CH$_2$); 2.70 ppm (t, 2H, CH$_2$); 4.15 ppm (q, 2H, OCH$_2$); 4.80 ppm (s, 2H, α-NH$_2^+$ and 1H, α-CH); 5.50 ppm (d, 1H, thiophene-H); 6.40 ppm (d, 1H, thiophene-H); 6.40 ppm (s, 1H, aryl-4-H); 6.72 ppm (s, 2H, aryl-2-H and aryl-6-H).

(3,5-Dichlorophenylamino)-(3-methylthiophen-2-yl)-acetic Acid Ethyl Ester (118)

δ=1.15 ppm (t, 3H, CH$_3$); 2.20 ppm (s, 3H, 2-CH$_3$-thiophene); 4.10 ppm (q, 2H, OCH$_2$); 5.50 ppm (d, 1H, α-CH); 6.65 ppm (s, 2H, aryl-2-H and aryl-6H); 6.80 ppm (d, 1H, thiophene-H); 7.28 ppm (d, 1H, thiophene-H).

(5-tert-Butylfuran-2-yl)-(3,5-dichlorophenylamino)-Acetic Acid (119)

δ=1.22 ppm (s, 9H, tert-Bu); 5.24 ppm (d, 1H, α-CH); 5.99 ppm (d, 1H, furan-H); 6.26 ppm (d, 1H, furan-H); 6.54 ppm (s, 1H, aryl-4-CH); 6.73 ppm (s, 2H, aryl-2H and aryl-6H); 8.27 ppm (d, 1H, α-NH); 13.80 ppm (s (broad), 1H, CO$_2$H).

(5-tert-Butyl-furan-2-yl)-(3,5-dichlorophenylamino)-acetic Acid Hydrochloride (119-HCl)

δ=1.25 ppm (s, 9H, tert-butyl); 5.30 ppm (m, 1H, α-CH); 6.00 ppm (d, 1H, furyl-H); 6.30 ppm (d, 1H, furyl-H); 6.65 ppm (m, 1H, α-NH); 6.70 ppm (s, 1H, aryl-H); 6.75 ppm (s, 2H, aryl-H).

(3,5-Dichlorophenylamino)-[5-(methylsulfanyl)methyl-furan-2-yl]-acetic Acid (106)

δ=2.02 ppm (s, 3H, SCH$_3$); 3.69 ppm (s, 2H, CH$_2$S); 5.30 ppm (d, 1H, α-CH); 6.22 ppm (s, 1H, furan-H); 6.37 ppm (s, 1H, furan-H); 6.63 ppm (s, 1H, aryl-4-H); 6.73 ppm (s, 2H, aryl-2-H and aryl-4H); 6.79 ppm (d, 1H, α-NH); 13.17 ppm (s (broad), 1H, CO$_2$H).

(3,5-Dichlorophenylamino)-[5-(methylsulfanyl)methyl-furan-2-yl]-acetic Acid Hydrochloride (106-HCl)

δ=2.08 ppm (s, 3H, SCH$_3$); 2.50 ppm (2, 2H, CH$_2$S); 3.70 ppm (s, 2H, α-NH$_2^+$); 5.37 ppm (m, 1H, α-CH); 6.25 ppm (d, 1H, furan-H); 6.40 ppm (d, 1H, furan-H); 6.80 ppm (s, 1H, aryl-4-H); 6.78 ppm (s, 2H, aryl-2-H and aryl-6-H).

(3,5-Dichlorophenylamino)-(5-methylsulfanylmethylfuran-2-yl)-acetic Acid Sodium Salt (106-Na)

δ=2.99 ppm (s, 3H, SCH$_3$); 3.65 ppm (s, 2H, CH$_2$S); 4.45 ppm (m, 1H, α-CH); 6.10 ppm (m, 3H, aryl-H); 6.45 ppm (m, 1H, α-NH); 6.50 ppm (d, 1H, thiophene-H); 6.55 ppm (d, 2H, thiophene-H).

(3,5-Dichlorophenylamino)-F5-(furan-2-ylmethylsulfanylmethyl)-furan-2-yl]-acetic Acid (122)

δ=3.68 ppm (s, 2H, CH$_2$S); 3.73 (s, 2H, CH$_2$S); 5.33 (d, 1H, α-CH); 5.72 ppm (m, 1H, furan-H); 6.26 ppm (d, 1H, furan-H); 6.27 ppm (d, 1H, furan-H); 6.36 ppm (d, 1H, furan-H); 6.39 ppm (d, 1H, furan-H); 6.64 ppm (s, 1H, aryl-4-H); 6.74 ppm (s, 2H, aryl-2-H and aryl-6-H); 7.55 ppm (d, 1H, α-NH); 13.23 ppm (s (broad), 1H, CO$_2$H).

(3,5-Dichlorophenylamino)-[5-(furan-2-ylmethyldisulfanylmethyl)-furan-2-yl]-acetic Acid (120)

δ=3.73 ppm (s, 2H, CH$_2$S); 3.80 ppm (s, 2H, CH$_2$S); 5.35 ppm (d, 1H, α-CH); 6.24 ppm (m, 1H, furan-H); 6.24 (d, 1H, furan-H); 6.30 ppm (d, 1H, furan-H); 6.38 ppm (s, 1H, furan-H); 6.43 ppm (d, 1H, furan-H); 6.43 ppm (s, 1H, aryl-4-H); 6.74 ppm (s, 2H, aryl-2-H and aryl-6-H); 7.58 ppm (d, 1H, α-NH); 13.20 ppm (s (broad), 1H, CO$_2$H).

(3,5-Dichlorophenylamino)-(5-methyldisulfanylmethylfuran-2-yl)-acetic Acid (121)

δ=2.08 ppm (s, 3H, SCH$_3$); 3.96 ppm (s, 2H, CH$_2$S); 5.30 (d, 1H, α-CH); 6.32 ppm (d, 1H, furan-H); 6.41 ppm (d, 1H, furan-H); 6.61 ppm (s, 1H, aryl-4-H); 6.73 ppm (s, 2H, aryl-2-H and aryl-6-H); 8.25 ppm (d, 1H, α-NH); 13.19 ppm (s (broad), 1H, CO$_2$H).

(5-Acetylsulfanylmethyl-furan-2-yl)-(3,5-dichlorophenylamino)-acetic Acid (110)

δ=2.35 ppm (s, 3H, COCH$_3$); 4.13 ppm (s, 2H, CH$_2$S); 5.28 ppm (d, 1H, α-CH); 6.24 ppm (s, 1H, furan-H); 6.35 (d, 1H, furan-H); 6.63 ppm (s, 1H, aryl-4-H); 6.71 ppm (s, 2H, aryl-2-H and aryl-6-H); 8.29 ppm (d, 1H, α-NH); 13.13 ppm (s (broad), 1H, CO$_2$H).

(5-Acetoxymethyl-furan-2-yl)-(3,5-dichlorophenylamino)-acetic Acid (123)

Molar mass (calc.): 358.18 g/mol; found 356.0

δ=2.05 ppm (s, 3H, COCH$_3$); 5.00 ppm (s, 2H, CH$_2$O); 5.20 ppm (m, 1H, α-CH); 6.40–6.50 ppm (m, 2H, furyl-H); 6.60 ppm (s, 1H, aryl-H); 6.65 ppm (s, 2H, aryl-H); 6.80 ppm (d, 1H, α-NH).

Further compounds prepared according to GWP 2 and GWP 3 are shown in Table 2.

TABLE 2

| Example No. | Compound | Molar mass calculated | Molar mass found |
|---|---|---|---|
| 106 | (3,5-Dichloro-phenylamino)-(5-methylsulfanyl-methyl-furan-2-yl)-acetic acid | 412.3 | 410.2 (M-H) 366.2 (M-CO$_2$) |
| 107 | (3,5-Dichloro-phenylamino)-(5-mercaptomethyl-furan-2-yl)-acetic acid | 332.2 | 330.1 (M-H) 286.1 (M-CO$_2$) |
| 108 | (3,5-Dichloro-phenylamino)-(5-methyl-thiophen-2-yl)-acetic acid | 316.2 | 314.0 (M-H) 270.2 (M-CO$_2$) |

TABLE 2-continued

| Example No. | Compound | Molar mass calculated | Molar mass found |
|---|---|---|---|
| 109 | (3,5-Dichloro-phenylamino)-(5-hydroxymethyl-thiophen-2-yl)-acetic acid | 332.2 | 331.9 (M-H) 286.1 (M-$CO_2$) |
| 110 | (5-Acetylsulfanylmethyl-furan-2-yl)-(3,5-dichloro-phenylamino)-acetic acid | 374.2 | 372.3 (M-H) 327.6 M-$CO_2$ |
| 111 | (3,5-Dichloro-phenylamino)-(5-ethyl-thiophen-2-yl)-acetic acid | 330.2 | 328.0 (M-H) 284.2 (M-$CO_2$) |
| 112 | (3,5-Dichloro-phenylamino)-(5-n-propyl-thiophen-2-yl)-acetic acid | 344.3 | 342.0 (M-H) 298.2 (M-$CO_2$) |

Example 3-General Working Procedure 4 (GWP 4)

The syntheses were carried out analogously to the synthesis process described by N. A. Petasis et al., *Tetrahedron* (1997), 16463–16470: 10 mmol of glyoxalic acid hydrate were dissolved in 50 ml of dichloromethane; 10 mmol of aniline component (II) and 10 mmol of the boronic acid of the furan or thiophene derivative (IV-A) or (IV-B) were added, with stirring, and stirring was carried out overnight at room temperature. The precipitated product was filtered off with suction and then washed with a small amount of cold dichloromethane, and the substance was dried under a high vacuum. Colorless solids were obtained.

The $^1$H-NMR data of some of the compounds prepared according to GWP 4 are shown hereinbelow; the NMR data were obtained at 300 MHz or 600 MHz, with $d_6$-DMSO being used as solvent:

(3,5-Dichlorophenylamino)-thiophen-3-yl)-acetic Acid (124)

Molar mass (calc.): 302.18 g/mol; found 301.9

δ=5.25 ppm (m, 1H, α-CH); 6.65 ppm (s, 1H, aryl-H); 6.70 ppm (s, 2H, aryl-H); 7.85 ppm (m, 1H, α-NH); 7.15 ppm (d, 1H, thiophene-H); 7.50–7.60 ppm (dd, 2H, thiophene-H); 13.00 (s (broad), 1H, COOH).

(3,5-Dichlorophenylamino)-(4-methylthiophen-2-yl)-acetic Acid (126)

Molar mass (calc.): 358.18 g/mol; found 317.1

δ=2.20 ppm (2, 3H, $CH_3$); 5.40 ppm (d, 1H, α-CH); 6.65 ppm (s, 1H, aryl-H); 6.75 ppm (s, 2H, aryl-H); 6.90 ppm (d, 1H, α-NH); 7.00–7.10 ppm (s, 2H, thiophene-H); 13.30 ppm (s (broad), 11H, COOH).

(3,5-Dichlorophenylamino)-(5-methylthiophen-2-yl)-acetic Acid (125)

Molar mass (calc.): 358.18 g/mol; found 316.2

δ=2.40 ppm (s, 3H, $CH_3$); 5.40 ppm (d, 1H, α-CH); 6.60–6.70 ppm (m, 2H, α-NH and aryl-H); 6.70 ppm (s, 2H, aryl-H); 6.90 ppm (d, 1H, thiophene-H); 6.95 ppm (d, 1H, thiophene-H); 13.30 ppm (s (broad), 1H, COOH).

(3,5-Dichlorophenylamino)-(5-methylthiophen-2-yl)-acetic Acid Sodium Salt (125-Na)

δ=2.40 ppm (s, 3H, $CH_3$); 5.30 ppm (d, 1H, α-CH); 6.60–6.80 ppm (m, 4H, α-NH and aryl-H); 6.85 ppm (d, 1H, thiophene-H); 6.90 ppm (d, 1H, thiophene-H).

(5-Chlorothiophen-2-yl)-(3,5-dichlorophenylamino)-acetic Acid (127)

Molar mass (calc.): 336.63 g/mol; found 335.7

δ=5.50 ppm (d, 1H, α-CH); 6.65 ppm (s, 1H, α-NH); 6.70 ppm (s, 1H, aryl-H); 6.80 ppm (s, 2H, aryl-H); 7.00 ppm (d, 1H, thiophene-H); 7.05 ppm (d, 1H, thiophene-H); 13.50 (s (broad), 1H, COOH).

(3,5-Dichlorophenylamino)-(5-chlorothiophen-2-yl)-acetic Acid Sodium Salt (127-Na)

δ=4.55 ppm (d, 1H, δ-CH); 6.55 ppm (s, 1H, aryl-H); 6.60 ppm (s, 2H, aryl-H); 6.75 ppm (d, 1H, thiophene-H); 6.85 ppm (d, 1H, thiophene-H).

Example 4-Receptor Binding Studies (Glycine Binding Site of the NMDA Receptor Channel)

The tests to determine the affinity of the compounds of formula (I) according to the invention for the glycine binding site of the NMDA receptor channel were carried out on brain membrane homogenates (homogenate of cortex and hippocampus area from the brains of male rats, Wistar strain) (B. M. Baron, B. W. Siegel, B. L. Harrison, R. S. Gross, C. Hawes and P. Towers, Journal of Pharmacology and Experimental Therapeutics, (1996), Vol. 279, p. 62).

To that end, cortex and hippocampus from freshly removed rat brains were exposed and homogenized, while cooling with ice, in 5 mmol/l of TRIS acetate buffer, 0.32 mmol/l of saccharose pH 7.4 (10 ml/g fresh weight) using a Potter homogenizer (Braun/Melsungen; 10 piston strokes at 500 rpm) and then centrifuged for 10 minutes at 1000 g and 4° C. The first supernatant was collected and the sediment was again homogenized, while cooling with ice, with 5 mmol/l of TRIS acetate buffer, 0.32 mol/l of saccharose pH 7.4 (5 ml/g original fresh weight) using the Potter homogenizer (10 piston strokes at 500 rpm) and centrifuged for 10 minutes at 1000 g and 4° C. The resulting supernatant was combined with the supernatant from the first centrifugation and centrifuged for 20 minutes at 17,000 g and 4° C. The supernatant from this centrifugation was discarded and the membrane sediment was taken up in 5 mmol/l of TRIS acetate buffer pH 8.0 (20 ml/g original fresh weight) and homogenized with 10 piston strokes at 500 rpm.

The membrane homogenate was then incubated for one hour at 4° C. and centrifuged for 30 minutes at 50,000 g and 4° C. The supernatant was discarded and the centrifuge tube containing the membrane sediment was closed with Parafilm and frozen for 24 hours at −20° C. On the following day, the membrane sediment was thawed and taken up in 5 mmol/l of ice-cold TRIS acetate buffer, 0.1% saponin (w/v) pH 7.0 (10 ml/g original fresh weight) and homogenized with 10 piston strokes at 500 rpm and then centrifuged for 20 minutes at 50,000 g and 4° C. The resulting supernatant was discarded and the sediment was taken up in a small volume in 5 mmol/l of TRIS acetate buffer pH 7.0 (about 2 ml/g original fresh weight) and again homogenized with 10 piston strokes at 500 rpm. After determination of the protein content, the membrane homogenate was adjusted to a protein concentration of 10 mg of protein/ml with 5 mmol/l TRIS acetate buffer pH 7.0, and was frozen in aliquots until testing.

For the receptor binding test, aliquots were thawed, diluted 1:10 with 5 mmol/l of TRIS acetate buffer pH 7.0, homogenized, while cooling with ice, with 10 piston strokes at 500 rpm using the Potter homogenizer (10 piston strokes at 500 rpm) and centrifuged for 60 minutes at 55,000 g and 4° C. The supernatant was decanted off and the membrane sediment was adjusted to a protein concentration of 1 mg/ml with 50 mmol/l of ice-cold TRIS acetate buffer pH 7.0 and again homogenized with 10 piston strokes at 500 rpm and maintained in suspension in an ice-bath while stirring with a magnetic stirrer. Of that membrane homogenate, 100 μl per 1 ml batch were used in the receptor binding test (0.1 mg protein/ml in the final batch).

In the binding test, 50 mmol/l of TRIS acetate buffer pH 7.0 were used as the buffer, and 1 nmol/l of ($^3$H)-MDL 105,519 (B. M. Baron et al. 1996) was used as the radioactive ligand. The proportion of non-specific binding was determined in the presence of 1 mmol/l of glycine.

In further batches, the compounds according to the invention were added in series of concentrations and the displacement of the radioactive ligand from its specific binding to the glycine binding site of the NMDA receptor channel was determined. The respective triplicate batches were incubated for 120 minutes at 4° C. and then harvested by means of filtration through glass fiber filter mats (GF/B) for determination of the radioactive ligand bonded to the membrane homogenate. The radioactivity retained on the glass fiber filters was measured after addition of scintillator in a β counter.

The affinity of the compounds according to the invention for the glycine binding site of the NMDA receptor channel was calculated as the $IC_{50}$ (concentration with 50% displacement of the radioactive ligand from its specific binding) by the law of mass action by means of non-linear regression and is shown in Table 3 after conversion (according to the Cheng-Prussoff equation) as the Ki value (mean+/−standard deviation of 3 independent tests) or as the percentage of the bonded radioactive ligand, see above, which is displaced from its specific binding at a concentration of 10 μM of the substance to be tested.

TABLE 3

| Example No. and Compound | | $K_i$ (μmol) | Glycine binding site of the NMDA receptor channel Displacement (%, 10 μmol) |
|---|---|---|---|
| 106 | (3,5-Dichloro-phenylamino)-5-(methylsulfanylmethyl-furan-2-yl)-acetic acid | | 65 |
| 106-HCl | (3,5-Dichloro-phenylamino)-(5-methylsulfanylmethyl-furan-2-yl)-acetic acid hydrochloride | | 91 |
| 106-Na | (3,5-Dichloro-phenylamino)-(5-methylsulfanylmethyl-furan-2-yl)-acetic acid sodium | 2.980 | 78 |
| 107 | (3,5-Dichloro-phenylamino)-(5-mercaptomethyl-furan-2-yl)-acetic acid | | 101 |
| 109 | (3,5-Dichloro-phenylamino)-(5-hydroxymethyl-thiophen-2-yl)-acetic acid | | 66 |
| 110 | (5-Acetylsulfanylmethyl-furan-2-yl)-(3,5-dichloro-phenylamino)-acetic acid | 0.120 | 104 |
| 111 | (3,5-Dichloro-phenylamino)-(5-ethyl-thiophen-2-yl)-acetic acid | | 44 |
| 113 | (3-Chloro-phenylamino)-(5-mercaptomethyl-furan-2-yl)-acetic acid | | 99 |
| 114 | (3,4-Dichloro-phenylamino)-(5-mercaptomethyl-furan-2-yl)-acetic acid | | 45 |
| 119-HCl | (5-tert-Butylfuran-2-yl)-(3,5-dichlorophenylamino)-acetic acid hydrochloride | | 91 |
| 120 | (3,5-Dichlorophenylamino)-[5-(furan-2-ylmethyl-disulfanylmethyl)-furan-2-yl]-acetic acid | 0.470 | 103 |
| 121 | (3,5-Dichlorophenylamino)-(5-methyldisulfanylmethyl-furan-2-yl)-acetic acid | 0.290 | 106 |
| 123 | (5-Acetoxymethylfuran-2-yl)-(3,5-dichlorophenylamino)-acetic acid | 5.03 | 60 |
| 125-Na | (3,5-Dichlorophenylamino)-(5-methylthiophen-2-yl)-acetic acid sodium salt | 5.03 | 63 |
| 126 | (3,5-Dichlorophenylamino)-(4-methylthiophen-2-yl)-acetic acid | 15.38 | 52 |
| 127 | (5-Chlorothiophen-2-yl)-(3,5-dichlorophenylamino)-acetic acid | 2.57 | 68 |
| 127-Na | (3,5-Dichlorophenylamino)-(5-chlorothiophen-2-yl)-acetic acid sodium salt | | 72 |

Example 5-Pharmaceutical Formulation of a Medicament According to the Invention 1 g of the hydrochloride of (3,5-dichlorophenylamino)-(5-methyldisulfanylmethylfuran-2-yl)-acetic acid (121) was dissolved at room temperature in 1 liter of water for injection purposes and then adjusted to isotonic conditions by addition of sodium chloride.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound of formula I, or a pharmaceutically acceptable salt thereof,

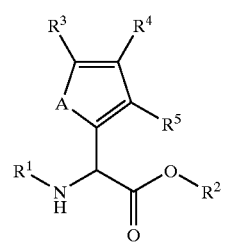

I wherein

A represents oxygen or sulfur, $R^1$ represents aryl, ($C_{1-6}$-alkyl)-aryl, heterocyclyl or ($C_{1-6}$-alkyl)-heterocyclyl, $R^2$ represents H, $C_{1-12}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl or ($C_{1-6}$-alkyl)-heterocyclyl, $R^3$, $R^4$ and $R^5$ each independently of the others represents H, OH, SH, F, Cl, Br, I, —CN, $NO_2$, $C_{1-12}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl, ($C_{1-6}$-alkyl)-heterocyclyl, —$SiR^6R^7R^8$, —$(CH_2)_n$—O—$(CH_2)_m$—$R^9$ wherein n=1, 2, 3 or 4 and m=0, 1, 2, 3 or 4, —$(CH_2)_o$—$S_p$—$(CH_2)_q$—$R^{10}$ wherein o=1, 2, 3 or 4, p=1 or 2 and q=0, 1, 2, 3 or 4, —$(CH_2)_r$—$CO_2R^{11}$ wherein r=0, 1, 2, 3 or 4, —$(CH_2)_s$—$OCOR^{12}$ wherein s=0, 1, 2, 3 or 4, or —C(=O)$R^{13}$, $R^6$, $R^7$ and $R^8$ each independently of the others represents $C_{1-6}$-alkyl or phenyl, $R^9$ and $R^{10}$ each independently of the other represents H, $CH_3$, aryl, heterocyclyl or —C(=O)—$C_{1-6}$-alkyl, —C(=O)—($C_{1-6}$-alkyl)-aryl or —C(=O)-aryl, $R^{11}$ represents H, $C_{1-6}$-alkyl or $CH_2$-phenyl, $R^{12}$ represents $C_{1-6}$-alkyl or aryl, $R^{13}$ represents H, $C_{1-6}$-alkyl, aryl, heterocyclyl or $NR^{14}R^{15}$, $R^{14}$ and $R^{15}$ each independently of the other represents H, $C_{1-6}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl or ($C_{1-6}$-alkyl)-heterocyclyl, or $R^{14}$ and $R^{15}$ together form —$(CH_2)_k$— wherein k=4, 5 or 6, wherein alkyl represents a non-cyclic hydrocarbon radical which is straight-chain or branched and is saturated or unsaturated and is unsubstituted or is monosubstituted or polysubstituted by identical or different substituents, cycloalkyl represents an alicyclic hydrocarbon radical which is saturated or unsaturated and is unsubstituted or is monosubstituted or polysubstituted by identical or different substituents, aryl is a radical selected from the group consisting of

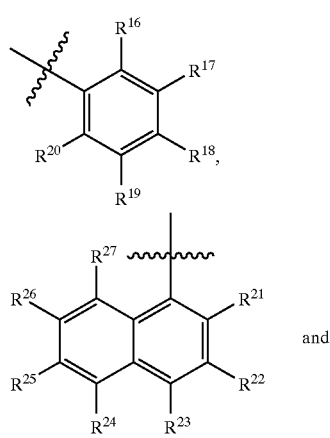

and

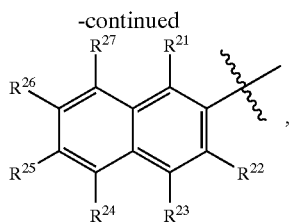

heterocyclyl represents a monocyclic or polycyclic radical in which at least one ring contains one hetero atom or 2, 3, 4 or 5 identical or different hetero atoms selected from the group consisting of N, O and S, the radical being saturated or unsaturated and being unsubstituted or monosubstituted or polysubstituted by identical or different substituents, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ each independently of the others represents H, $OR^{28}$, $S(O)_tR^{29}$ wherein t=0, 1 or 2, $SO_2OR^{30}$, F, Cl, Br, I, —CN, $NO_2$, $C_{1-12}$-alkyl, $C_{3-8}$-cycloalkyl, ($C_{1-6}$-alkyl)-$C_{3-8}$-cycloalkyl, phenyl or ($C_{1-6}$-alkyl)-phenyl, wherein phenyl is unsubstituted or is monosubstituted or polysubstituted by identical or different substituents, heterocyclyl, ($C_{1-6}$-alkyl)-heterocyclyl, —$CO_2R^{31}$ or —$NR^{32}R^{33}$, $R^{28}$, $R^{29}$, $R^{30}$ and $R^{31}$ each independently of the others represents H, $C_{1-12}$-alkyl, $C_{3-8}$-cycloalkyl, ($C_{1-6}$-alkyl)-$C_{3-8}$-cycloalkyl, phenyl or ($C_{1-6}$-alkyl)-phenyl, wherein phenyl is unsubstituted or is monosubstituted or polysubstituted by identical or different substituents, heterocyclyl, ($C_{1-6}$-alkyl)-heterocyclyl or —$NR^{34}R^{35}$, $R^{32}$ and $R^{33}$ each independently of the other represents H, $C_{1-6}$-alkyl, $C_{3-8}$-cycloalkyl, ($C_{1-6}$-alkyl)-$C_{3-8}$-cycloalkyl, phenyl, ($C_{1-6}$-alkyl)-phenyl, heterocyclyl or ($C_{1-6}$-alkyl)-heterocyclyl, or $R^{32}$ and $R^{33}$ together form —$(CH_2)_h$— wherein h=4, 5 or 6, and $R^{34}$ and $R^{35}$ each independently of the other represents H, $C_{1-6}$-alkyl, $C_{3-8}$-cycloalkyl, ($C_{1-6}$-alkyl)-$C_{3-8}$-cycloalkyl, phenyl, ($C_{1-6}$-alkyl)-phenyl, heterocyclyl or ($C_{1-6}$-alkyl)-heterocyclyl, or $R^{34}$ and $R^{35}$ together form —$(CH_2)_g$— wherein g=4, 5 or 6, Provided that (4-methoxy-phenylamino)-thien-2-yl-acetic acid is excluded, wherein the compound is in the form of a racemate, a pure enantiomer, a pure diastereoisomer, a mixture of enantiomers or diastereoisomers in any mixing ratio.

2. A compound according to claim 1, or a pharmnaceutically acceptable salt thereof, wherein $R^1$ represents aryl or heterocyclyl$^1$, $R^2$ represents H, $C_{1-12}$-alkyl, ($C_{1-6}$-alkyl)-$C_{3-8}$-cycloalkyl, aryl or ($C_{1-6}$-alkyl)-aryl, $R^3$, $R^4$ and $R^5$ each independently of the others represents H, OH, SH, Cl, Br, $C_{1-12}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl$^1$, ($C_{1-6}$-alkyl)-heterocyclyl$^1$, —$SiR^6R^7R^8$, —$(CH_2)_n$—O—$(CH_2)_m$—$R^9$ wherein n=1, 2, 3 or 4 and m=0, 1 or 2, —$(CH_2)_o$—$S_p$—$(CH_2)_q$—$R^{10}$ wherein o=1, 2, 3 or 4, p =1 or 2 and q 0, 1 or 2, —$(CH_2)_r$—$CO_2R^{11}$ wherein r=0, 1, 2 or 3, —$(CH_2)_s$—OC(=O)$R^{12}$ wherein s=0, 1 or 2, or —C(=O)$R^{13}$, $R^6$, $R^7$ and $R^8$ each independently of the others represents $C_{1-6}$-alkyl or phenyl, $R^9$ and $R^{10}$ each independently of the other represents H, $CH_3$, aryl, heterocyclyl or —C(=O)—$C_{1-6}$-alkyl, —C(=O)—($C_{1-6}$-alkyl)-aryl or —C(=O)-aryl, $R^{11}$ represents H, $C_{1-6}$-alkyl or $CH_2$-phenyl,
$R^{12}$ represents $C_{1-6}$-alkyl or aryl,
$R^{13}$ represents $C_{1-6}$-alkyl or aryl,

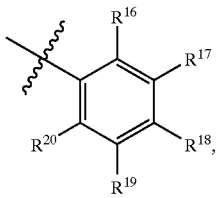

wherein aryl represents
heterocyclyl$^1$ represents a monocyclic or bicyclic organic radical in which at least one ring is 5- or 6-membered and contains one hetero atom or 2 identical or different hetero atoms selected from the group consisting of N, O and S, the radical being saturated or unsaturated and being unsubstituted or monosubstituted or polysubstituted by identical or different substituents,
$R^{16}$, $R^{17}$, $R^{18}$, $R^{19}$ and $R^{20}$ each independently of the others represents H, $OR^{28}$, $S(O)_tR^{29}$ wherein t=0 or 2, $SO_2OR^{30}$, F, Cl, Br, I, —CN, $NO_2$, $C_{1-12}$-alkyl, $C_{3-8}$-cycloalkyl, ($C_{1-6}$-alkyl)-$C_{3-8}$-cycloalkyl, phenyl or ($C_{1-6}$-alkyl)-phenyl, wherein phenyl is unsubstituted or is monosubstituted or polysubstituted by identical or different substituents, heterocyclyl$^1$, ($C_{1-6}$-alkyl)-heterocyclyl$^1$, —$CO_2R^{31}$ or —$NR^{32}R^{33}$,
$R^{28}$, $R^{29}$, $R^{30}$ and $R^{31}$ each independently of the others represents H, $C_{1-6}$-alkyl or phenyl, and
$R^{32}$ and $R^{33}$ each independently of the other represents H, $C_{1-6}$-alkyl, ($C_{1-6}$-alkyl)-phenyl, or $R^{32}$ and $R^{33}$ together form —$(CH_2)_h$— wherein h=4, 5 or 6.

3. A compound according to claim 2, or a pharmaceutically acceptable salt thereof, wherein
$R^1$ represents aryl or heterocyclyl$^2$,
$R^2$ represents H, methyl, ethyl, n-propyl, 2-propyl, n-butyl, tert-butyl, n-hexyl,
$R^3$, $R^4$ and $R^5$ each independently of the others represents H, OH, SH, Br, Cl, $C_{1-6}$-alkyl, 2-furyl, 3-furyl, 2-thienyl, 3-thienyl, —$SiR^6R^4R^8$, —$CH_2OH$, —$CH_2$—O—(C=O)—$CH_3$, —$(CH_2)$—$S_p$—$(CH_2)_q$—$R^{10}$ wherein p=1 or 2 and q=0 or 1, —$(CH_2)_r$—$CO_2R^{11}$ wherein r=0 or 1, or —$COR^{13}$,
$R^6$, $R^7$ and $R^8$ each independently of the others represents methyl, tert-butyl or phenyl,
$R^{10}$ represents H, methyl, ethyl, n-propyl, 2-furyl, 2-thienyl or —C(=O)—$CH_3$,
$R^{11}$ represents H, methyl, ethyl or tert-butyl,
$R^{13}$ represents methyl,

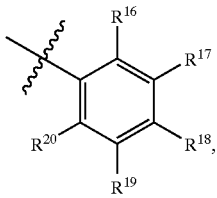

wherein aryl represents

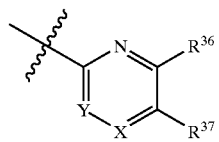 or 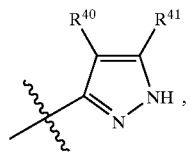

heterocyclyl$^2$ represents
$R^{16}$, $R^{17}$, $R^{18}$, $R^{19}$ and $R^{20}$ each independently of the others represents H, $OR^{28}$, $S(O)_tR^{29}$ wherein t=0, F, Cl, Br, I, —CN, —$NO_2$, methyl, ethyl, n-propyl, 2-propyl, n-butyl, 2-butyl, isobutyl, tert-butyl, n-pentyl, neopentyl, isopentyl, n-hexyl, isohexyl, $CF_3$ or —$CO_2R^{31}$,
$R^{28}$, $R^{29}$ and $R^{31}$ each independently of the others represents H, methyl, ethyl, —$CF_3$ or phenyl,
X-Y represents $CR^{38}$—$CR^{39}$, $CR^{38}$—N or N—$CR^{39}$,
$R^{36}$, $R^{37}$, $R^{38}$ and $R^{39}$ each independently of the others represents H, F, Cl, Br, I, —CN, —$NO_2$, —OH, —SH, $C_{1-6}$-alkyl or —$CF_3$, and
$R^{40}$ and $R^{41}$ each independently of the other represents H, F, Cl, Br, I, —CN, —OH, —O—$C_{1-6}$-alkyl, —SH, —S—$C_{1-6}$-alkyl, $C_{1-6}$-alkyl, $CO_2$—$C_{1-6}$-alkyl or —N=N-aryl.

4. A compound according to claim 3, or a pharmaceutically acceptable salt thereof, wherein
$R^1$ represents aryl or heterocyclyl$^2$,
$R^2$ represents H, methyl, ethyl or tert-butyl,
$R^3$ represents H, Cl, methyl, ethyl, n-propyl, 2-propyl, n-butyl, tert-butyl, —$CH_2OH$, —$CH_2SH$, —$CH_2$—S—$CH_3$, —$CH_2$—S—$CH_2$-furan-2-yl, —$CH_2$—O—(C=O)—$CH_3$, —$CH_2$—S—(C=O)—$CH_3$, —$CH_2$—S—S—$CH_3$, —$CH_2$—S—S—$CH_2$-furan-2-yl, —$CH_2$—$CO_2$methyl or —$CH_2$—$CO_2$ethyl,
$R^4$ represents H, Br, methyl, ethyl, —$CH_2OH$, —$CO_2$methyl, —$CO_2$ethyl or C(=O)methyl,
$R^5$ represents H, methyl or ethyl,

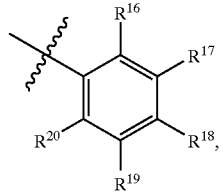

wherein aryl represents

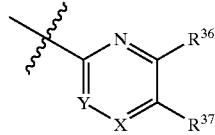 or 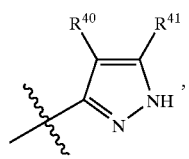

heterocyclyl$^2$ represents
$R^{16}$ represents H, —O-phenyl, F, Cl, Br, methyl, ethyl, n-propyl, 2-propyl or tert-butyl,
$R^{17}$ represents H, Cl, methyl, ethyl or $CF_3$,
$R^{18}$ represents H, F, Cl, Br, I, —CN, —O—$CH_3$, —O—$CF_3$, —O-phenyl, methyl, ethyl, n-propyl, 2-propyl, n-butyl, 2-butyl or tert-butyl, R$^{19}$ represents H, Cl, Br, methyl or ethyl,
R$^{20}$ represents H or methyl,
X-Y represents CR$^{38}$═CR$^{39}$, CR$^{33}$—N or N—CR$^{39}$,
R$^{36}$ represents H, methyl or ethyl,
R$^{37}$ represents H, NO$_2$, Cl, Br, methyl or CF$_3$,
R$^{38}$ represents H,
R$^{39}$ represents H, Cl or Br,
R$^{40}$ represents H, —N═N-phenyl, —CN, CO$_2$H, CO$_2$-methyl or CO$_2$-ethyl, and
R$^{41}$ represents H, OH, SH, S-methyl, methyl, ethyl, n-propyl, 2-propyl, n-butyl or tert-butyl.

5. A compound according claim 4, or a pharmaceutically acceptable salt thereof, wherein
R$^1$ represents 4-trifluoromethoxy-phenyl, 2-phenoxy-phenyl, 4-phenoxy-phenyl, 2-chloro-phenyl, 4-chloro-phenyl, 4-iodo-phenyl, 4-cyano-phenyl, 2-methyl-phenyl, 2-ethyl-phenyl, 4-ethyl-phenyl, 2-(2-propyl)-phenyl, 4-(2-butyl)-phenyl, 4-tert-butyl-phenyl, 2,4-dichlorophenyl, 2,3-dichlorophenyl, 3,5-dichlorophenyl, 2,4-dibromo-phenyl, 4-chloro-2-fluoro-phenyl, 2-chloro-4-fluoro-phenyl, 4-bromo-2-chloro-phenyl, 2-chloro-4-iodo-phenyl, 3-chloro-2-methyl-phenyl, 4-chloro-2-methyl-phenyl, 5-chloro-2-methyl-phenyl, 2-chloro-4-methyl-phenyl, 4-chloro-3-trifluoromethyl-phenyl, 2,4-dibromo-5-methyl-phenyl, 5-nitro-pyridin-2-yl, 3,5-dibromo-pyridin-2-yl, 3,5-dichloro-pyridin-2-yl, 3-chloro-5-trifluoromethyl-pyridin-2-yl, 3,5-dibromo-6-methyl-pyridin-2-yl, pyrazin-2-yl, 5-bromo-pyrimidin-2-yl, 4-carboxyethyl-pyrazol-3-yl, 4-cyano-pyrazol-3-yl, 5-tert-butyl-pyrazol-3-yl, 5-hydroxy-4-(4-phenylazo)-pyrazol-3-yl or 4-cyano-5-methylsulfanyl-pyrazol-3-yl,
R$^2$ represents H or ethyl,
R$^3$ represents H, Cl, methyl, ethyl, n-propyl, tert-butyl, —CH$_2$OH, —CH$_2$SH, —CH$_2$S—CH$_3$, —CH$_2$—S—CH$_2$-furan-2-yl, —CH$_2$—O—(C═O)—CH$_3$, —CH$_2$—S—(C═O)—CH$_3$—, —CH$_2$—S—S—CH$_3$, —CH$_2$—S—S—CH$_2$-furan-2-yl or —CH$_2$—CO$_2$ethyl,
R$^4$ represents H, Br, methyl, —CH$_2$OH, —CO$_2$methyl, —CO$_2$ethyl or —C(═O)CH$_3$,
R$^5$ represents H or methyl.

6. A compound according to claim 5, or a pharmaceutically acceptable salt thereof, wherein
R$^1$ represents 3,5-dichlorophenyl and
R$^2$ represents H.

7. A compound according to claim 1, or a pharmaceutically acceptable salt thereof, wherein the compound is selected from the group consisting of
(5-methylsulfanylmethyl-furan-2-yl)-(5-nitro-pyridin-2-ylamino)-acetic acid,
(5-bromopyrimidin-2-ylamino)-(5-methylsulfanylmethyl-furan-2-yl)-acetic acid,
5-[carboxy-(3,5-dichloropyridin-2-ylamino)-methyl]-2-methyl-furan-3-carboxylic acid ethyl ester,
5-[carboxy-(3,5-dibromopyridin-2-ylamino)-methyl]-2-methyl-furan-3-carboxylic acid ethyl ester,
5-[carboxy-(3,5-dibromo-6-methyl-pyridin-2-ylamino)-methyl]-2-methyl-furan-3-carboxylic acid ethyl ester,
(3,5-dibromo-6-methyl-pyridin-2-ylamino)-(4-hydroxymethyl-furan-2-yl)-acetic acid,
(3,5-dichloro-pyridin-2-ylamino)-(4-methyl-thiophen-2-yl)-acetic acid,
(2,4-dibromo-5-methyl-phenylamino)-(4-methyl-thiophen-2-yl)-acetic acid,
(4-methyl-thiophen-2-yl)-(5-nitro-pyridin-2-ylamino)-acetic acid,
(3,5-dichloro-pyridin-2-ylamino)-furan-2-yl-acetic acid,
(3,5-dibromopyridin-2-ylamino)-furan-2-yl-acetic acid,
(3,5-dibromo-6-methyl-pyridin-2-ylamino)-furan-2-yl-acetic acid,
(3-chloro-5-trifluoromethyl-pyridin-2-ylamino)-furan-2-yl-acetic acid,
(5-bromopyrimidin-2-ylamino)-furan-2-yl-acetic acid,
5-[(3,5-dichloro-phenylamino)-ethoxycarbonyl-methyl]-2-methyl-furan-3-carboxylic acid methyl ester,
(5-hydroxy-4-phenylazo-1H-pyrazol-3-ylamino)-(5-methylsulfanylmethyl-furan-2-yl)-acetic acid ethyl ester,
3-{[ethoxycarbonyl-(4-ethoxycarbonyl-5-methyl-furan-2-yl)-methyl]-amino}-1H-pyrazole-4-carboxylic acid ethyl ester,
5-[(4-cyano-5-methylsulfanyl-1H-pyrazol-3-ylamino)-ethoxycarbonyl-methyl]-2-methyl-furan-3-carboxylic acid ethyl ester,
5-[(4-cyano-1H-pyrazol-3-ylamino)-ethoxycarbonyl-methyl]-2-methyl-furan-3-carboxylic acid ethyl ester,
5-[(4-bromo-2-chloro-phenylamino)-ethoxycarbonyl-methyl]-2-methyl-furan-3-carboxylic acid ethyl ester,
5-[(4-cyano-phenylamino)-ethoxycarbonyl-methyl]-2-methyl-furan-3-carboxylic acid ethyl ester,
(4-hydroxymethyl-furan-2-yl)-(5-hydroxy-4-phenylazo-1H-pyrazol-3-ylamino)-acetic acid ethyl ester,
(4-cyano-5-methylsulfanyl-1H-pyrazol-3-ylamino)-(4-hydroxymethyl-furan-2-yl)-acetic acid ethyl ester,
(4-bromo-2-chloro-phenylamino)-(4-hydroxymethyl-furan-2-yl)-acetic acid ethyl ester,
(3,5-dichloro-phenylamino)-(4-hydroxymethyl-furan-2-yl)-acetic acid ethyl ester,
(5-chloro-2-methyl-phenylamino)-[5-(furan-2-ylmethylsulfanylmethyl)-furan-2-yl]-acetic acid ethyl ester,
(2,4-dibromo-phenylamino)-(4-methyl-thiophen-2-yl)-acetic acid,
(5-chloro-2-methyl-phenylamino)-(5-methylsulfanylmethyl-furan-2-yl)-acetic acid,
(2-ethyl-phenylamino)-(5-methylsulfanylmethyl-furan-2-yl)-acetic acid,
(4-sec-butyl-phenylamino)-(5-methylsulfanylmethyl-furan-2-yl)-acetic acid,
(5-methylsulfanylmethyl-furan-2-yl)-(4-trifluoromethoxy-phenylamino)-acetic acid,
(2-isopropyl-phenylamino)-(5-methylsulfanylmethyl-furan-2-yl)-acetic acid,
(2,4-dibromo-phenylamino)-(5-methylsulfanylmethyl-furan-2-yl)-acetic acid,
(4-tert-butyl-phenylamino)-(5-methylsulfanylmethyl-furan-2-yl)-acetic acid,
(5-chloro-2-methyl-phenylamino)-[5-(furan-2-ylmethylsulfanylmethyl)-furan-2-yl]-acetic acid,
(2-ethyl-phenylamino)-[5-(furan-2-ylmethylsulfanylmethyl)-furan-2-yl]-acetic acid,
(4-sec-butyl-phenylamino)-[5-(furan-2-ylmethylsulfanylmethyl)-furan-2-yl]-acetic acid,
[5-(furan-2-ylmethylsulfanylmethyl)-furan-2-yl]-(2-isopropyl-phenylamino)-acetic acid,
(4-tert-butyl-phenylamino)-[5-(furan-2-ylmethylsulfanylmethyl)-furan-2-yl]-acetic acid, 5-[ethoxycarbonyl-(4-Iodo-phenylamino)-methyl]-2-methyl-furan-3-carboxylic acid methyl ester, 5-[(4-chloro-2-methyl-phenylamino)-ethoxycarbonyl-methyl]-2-methyl-furan-3-carboxylic acid methyl ester, 5-[ethoxycarbonyl-(4-phenoxy-phenylamino)-methyl]-2-methyl-furan-3-carboxylic acid methyl ester, 5-[ethoxycarbonyl-(4-iodo-phenylamino)-methyl]-2-methyl-furan-3-carboxylic acid ethyl ester, 5-[(2-chloro-phenylamino)-ethoxycarbonyl-methyl]-2-methyl-furan-3-carboxylic acid ethyl ester, 5-[(4-chloro-2-methyl-phenylamino)-ethoxycarbonyl-methyl]-2-methyl-furan-3-carboxylic acid ethyl ester, 5-[(2-chloro-4-fluoro-phenylamino)-ethoxycarbonyl-methyl]-2-methyl-furan-3-carboxylic acid ethyl ester, 5-[ethoxycarbonyl-(4-phenoxy-phenylamino)-methyl]-2-methyl-furan-3-carboxylic acid ethyl ester, 5-[(2,3-dichloro-phenylamino)-ethoxycarbonyl-methyl]-2-methyl-furan-3-carboxylic acid ethyl ester, (4-hydroxymethyl-furan-2-yl)-(4-iodo-phenylamino)-acetic acid ethyl ester, (2,4-dichloro-phenylamino)-(4-hydroxymethyl-furan-2-yl)-acetic acid ethyl ester, (4-chloro-2-methyl-phenylamino)-(4-hydroxymethyl-furan-2-yl)-acetic acid ethyl ester, (4-hydroxymethyl-furan-2-yl)-(4-phenoxy-phenylamino)-acetic acid ethyl ester, (2,3-dichloro-phenylamino)-(4-hydroxymethyl-furan-2-yl)-acetic acid ethyl ester, (2,3-dichloro-phenylamino)-furan-2-yl-acetic acid ethyl ester, 5-[carboxy-(3,5-dibromo-6-methyl-pyridin-2-ylamino)-methyl]-2-methyl-furan-3-carboxylic acid methyl ester, (5-methylsulfanylmethyl-furan-2-yl)-(pyrazin-2-ylamino)-acetic acid, (3,5-dibromo-pyridin-2-ylamino)-(5-methylsulfanylmethyl-furan-2-yl)-acetic acid, (3,5-dibromo-6-methyl-pyridin-2-ylamino)-(5-methylsulfanylmethyl-furan-2-yl)-acetic acid, 5-[(4-bromo-2-chloro-phenylamino)-carboxy-methyl]-2-methyl-furan-3-carboxylic acid methyl ester, 5-[carboxy-(4-cyano-phenylamino)-methyl]-2-methyl-furan-3-carboxylic acid methyl ester, 5-[carboxy-(3,5-dichloro-phenylamino)-methyl]-2-methyl-furan-3-carboxylic acid methyl ester, 5-[carboxy-(2-phenoxy-phenylamino)-methyl]-2,4-dimethyl-furan-3-carboxylic acid ethyl ester, 5-[(4-bromo-2-chloro-phenylamino)-carboxy-methyl]-2,4-dimethyl-furan-3-carboxylic acid ethyl ester, 5-[carboxy-(4-cyano-phenylamino)-methyl]-2,4-dimethyl-furan-3-carboxylic acid ethyl ester, 5-[carboxy-(3,5-dichloro-phenylamino)-methyl]-2,4-dimethyl-furan-3-carboxylic acid ethyl ester, 5-[(4-bromo-2-chloro-phenylamino)-carboxy-methyl]-2-methyl-furan-3-carboxytic acid ethyl ester, 5-[carboxy-(4-cyano-phenylamino)-methyl]-2-methyl-furan-3-carboxylic acid ethyl ester, 5-[carboxy-(3,5-dichloro-phenylamino)-methyl]-2-methyl-furan-3-carboxylic acid ethyl ester, (5-tert-butyl-1H-pyrazol-3-ylamino)-(4-hydroxymethyl-furan-2-yl)-acetic acid, (4-bromo-2-chloro-phenylamino)-(3-methyl-thiophen-2-yl)-acetic acid, (4-cyano-phenylamino)-(3-methyl-thiophen-2-yl)-acetic acid, (3,5-dichloro-phenylamino)-(3-methyl-thiophen-2-yl)-acetic acid, (3,5-dichloro-phenylamino)-furan-2-yl-acetic acid,

[5-(furan-2-ylmethylsulfanylmethyl)-furan-2-yl]-(4-phenoxy-phenylamino)-acetic acid ethyl ester, (5-ethoxycarbonylmethyl-thiophen-2-yl)-(5-hydroxy-4-phenylazo-1H-pyrazol-3-ylamino)-acetic acid, ethyl ester, {5-[1-(4-cyano-1H-pyrazol-3-ylamino)-3-methoxy-2-oxo-propyl]-thiophen-2-yl}-acetic acid ethyl ester, (4-ethyl-phenylamino)-(5-methylsulfanylmethyl-furan-2-yl)-acetic acid, (3-chloro-2-methyl-phenylamino)-(5-methylsulfanylmethyl-furan-2-yl)-acetic acid, (4-chloro-phenylamino)-(5-methylsulfanylmethyl-furan-2-yl)-acetic acid, (5-methylsulfanylmethyl-furan-2-yl)-o-tolylamino-acetic acid, 5-[carboxy-(4-chloro-3-trifluoromethyl-phenylamino)-methyl]-2-methyl-furan-3-carboxylic acid ethyl ester, 5-[carboxy-(2-chloro-phenylamino)-methyl]-2-methyl-furan-3-carboxylic acid ethyl ester, 5-[carboxy-(2-chloro-4-fluoro-phenylamino)-methyl]-2-methyl-furan-3-carboxylic acid ethyl ester, 5-[carboxy-(4-chloro-2-fluoro-phenylamino)-methyl]-2-methyl-furan-3-carboxylic acid ethyl ester, 5-[carboxy-(2,3-dichloro-phenylamino)-methyl]-2-methyl-furan-3-carboxylic acid ethyl ester, (2,4-dichloro-phenylamino)-(4-methyl-thiophen-2-yl)-acetic acid, (4-chloro-3-trifluoromethyl-phenylamino)-(4-methyl-thiophen-2-yl)-acetic acid, (2,4-dichloro-phenylamino)-furan-2-yl-acetic acid, (4-chloro-3-trifluoromethyl-phenylamino)-furan-2-yl-acetic acid, (4-iodo-phenylamino)-(5-methylsulfanylmethyl-furan-2-yl)-acetic acid, (2,4-dichloro-phenylamino)-(5-methylsulfanylmethyl-furan-2-yl)-acetic acid, (4-chloro-3-trifluoromethyl-phenylamino)-(5-methylsulfanylmethyl-furan-2-yl)-acetic acid, (2-chloro-phenylamino)-(5-methylsulfanylmethyl-furan-2-yl)-acetic acid, (4-chloro-2-methyl-phenylamino)-(5-methylsulfanylmethyl-furan-2-yl)-acetic acid, (2-chloro-4-fluoro-phenylamino)-(5-methylsulfanylmethyl-furan-2-yl)-acetic acid, (2-chloro-4-methyl-phenylamino)-(5-methylsulfanylmethyl-furan-2-yl)-acetic acid, (2,3-dichloro-phenylamino)-(5-methylsulfanylmethyl-furan-2-yl)-acetic acid,

[5-(furan-2-ylmethylsulfanylmethyl)-furan-2-yl]-(4-iodo-phenylamino)-acetic acid, (4-chloro-3-trifluoromethyl-phenylamino)-[5-(furan-2-ylmethylsulfanylmethyl)-furan-2-yl]-acetic acid, (4-chloro-2-methyl-phenylamino)-[5-(furan-2-ylmethylsulfanylmethyl)-furan-2-yl]-acetic acid, (2-chloro-4-methyl-phenylamino)-[5-(furan-2-ylmethylsulfanylmethyl)-furan-2-y]-acetic acid,
(4-chloro-3-trifluoromethyl-phenylamino)-(5-ethoxycarbonylmethyl-thiophen-2-yl)-acetic acid,
(4-acetyl-3,5-dimethyl-furan-2-yl)-(2-chloro-4-methyl-phenylamino)-acetic acid,
(4-acetyl-3,5-dimethyl-furan-2-yl)-(2,3-dichloro-phenylamino)-acetic acid,
(3,5-dichloro-phenylamino)-(5-methylsulfanylmethyl-furan-2-yl)-acetic acid,
(3-chloro-phenylamino)-(5-mercaptomethyl-furan-2-yl)-acetic acid,
(3,4-dichloro-phenylamino)-(5-mercaptomethyl-furan-2-yl)-acetic acid,
(3,5-dichloro-phenylamino)-(5-mercaptomethyl-furan-2-yl)-acetic acid,
(3,5-dichloro-phenylamino)-(5-methyl-thiophen-2-yl)-acetic acid,
(3,5-dichloro-phenylamino)-(5-hydroxymethyl-thiophen-2-yl)-acetic acid,
(5-acetylsulfanylmethyl-furan-2-yl)-(3,5-dichloro-phenylamino)-acetic acid,
(3,5-dichloro-phenylamino)-(5-ethyl-thiophen-2-yl)-acetic acid,
(3,5-dichloro-phenylamino)-(5-n-propyl-thiophen-2-yl)-acetic acid,
(3,5-dichloro-phenylamino)-[5-(furan-2-ylmethylsulfanylmethyl)-furan-2-yl]-acetic acid,
(3-chloro-phenylamino)-(5-mercaptomethyl-furan-2-yl)-acetic acid,
(3,4-dichloro-phenylamino)-(5-mercaptomethyl-furan-2-yl)-acetic acid,
(3,5-dichloro-phenylamino)-(thiophen-2-yl)-acetic acid ethyl ester,
(4-bromofuran-2-yl)-(3,5-dichloro-phenylamino)-acetic acid ethyl ester,
(3,5-dichloro-phenylamino)-(5-propylthiophen-2-yl)-acetic acid ethyl ester,
(3,5-dichloro-phenylamino)-(3-methylthiophen-2-yl)-acetic acid ethyl ester,
(5-tert-butylfuran-2-yl)-(3,5-dichloro-phenylamino)-acetic acid,
(3,5-dichlorophenylamino)-[5-(furan-2-ylmethyldisulfanylmethyl)-furan-2-yl]-acetic acid,
(3,5-dichlorophenylamino)-(5-methyldisulfanylmethylfuran-2-yl)-acetic acid,
(3,5-dichlorophenylamino)-[5-(furan-2-ylmethylsulfanylmethyl)-furan-2-yl]-acetic acid,
5-acetoxymethylfuran-2-yl-(3,5-dichlorophenylamino)-acetic acid,
(3,5-dichlorophenylamino)-thiophen-3-yl-acetic acid,
(3,5-dichlorophenylamino)-(5-methylthiophen-2-yl)-acetic acid,
(3,5-dichlorophenylamino)-(4-methylthiophen-2-yl)-acetic acid, and
(5-chlorothiophen-2-yl)-(3,5-dichlorophenylamino)-acetic acid.

8. A method for the preparation of a compound according to claim 1, comprising reacting an amine of formula II $$R^1-NH_2 \quad\quad II$$

in the presence of an acid, with a glyoxalic acid derivative of formula III

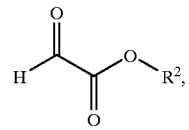

and with a heterocycle of formula IV

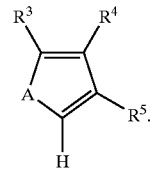

9. A method according to claim 8, which is carried out as a one-pot reaction.
10. A method according to claim 8, wherein the reaction of the compounds (II), (III) and (IV) is carried out under the action of microwave radiation.
11. A method according to claim 9, wherein the reaction of the compounds of formulae II, III and IV is carried out under the action of microwave radiation.
12. A method according to claim 8, wherein the reaction is carried out in an organic solvent at a temperature of from about 0° C. to 100° C.
13. A method according to claim 12, wherein the reaction is carried out at a temperature of from about 15° C. to 50° C.
14. A pharmaceutical composition comprising a compound of formula I, or a pharmaceutically acceptable salt thereof,

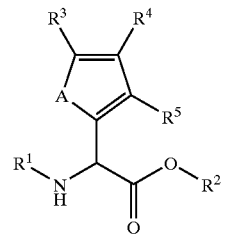

wherein
A represents oxygen or sulfur,
$R^1$ represents aryl, ($C_{1-6}$-alkyl)-aryl, heterocyclyl or ($C_{1-6}$-alkyl)-heterocyclyl,
$R^2$ represents H, $C_{1-2}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl or ($C_{1-6}$-alkyl)-heterocyclyl,
$R^3$, $R^4$ and $R^5$ each independently of the others represents H, OH, SH, F, Cl, Br, I, —CN, $NO_2$, $C_{1-12}$-alkyl, $C_{3-8}$-cycloalkyl, ($C_{1-6}$-alkyl)-$C_{3-8}$-cycloalkyl, aryl, ($C_{1-6}$-alkyl)-aryl, heterocyclyl, ($C_{1-6}$-alkyl)-heterocyclyl, —$SiR^6R^7R^8$, $(CH_2)_n$—, —$(CH_2)_m$—$R^9$ wherein n=1, 2, 3 or 4 and m=0, 1, 2, 3 or 4, —$(CH_2)_o$—$S_p$—$(CH_2)_q$—$R^{10}$ wherein o=1, 2, 3 or 4, p=1 or 2 and q=0, 1, 2, 3 or 4, $(CH_2)_r$—$CO_2R^{11}$ wherein r=0, 1, 2, 3 or 4, —$(CH_2)_s$—$OCOR^{12}$ wherein s=0, 1, 2, 3 or 4, or —$COR^{13}$,
$R^6$, $R^7$ and $R^8$ each independently of the others represents $C_{1-6}$-alkyl or phenyl, R$^9$ and R$^{10}$ each independently of the other represents H, CH$_3$, aryl, heterocyclyl or —C(=O)—C$_{1-6}$-alkyl, —C(=O)—(C$_{1-16}$-alkyl)-aryl or —C(=O)-aryl, R$^{11}$ represents H, C$_{1-6}$-alkyl or CH$_2$-phenyl, R$^{12}$ represents C$_{1-6}$-alkyl or aryl, R$^{13}$ represents H, C$_{1-6}$-alkyl, aryl, heterocyclyl or NR$^{14}$R$^{15}$, R$^{14}$ and R$^{15}$ each independently of the other represents H, C$_{1-6}$-alkyl, C$_{3-8}$-cycloalkyl, (C$_{1-6}$-alkyl)-C$_{3-6}$-cycloalkyl, aryl, (C$_{1-6}$-alkyl)-aryl, heterocyclyl or (C$_{1-6}$-alkyl)-heterocyclyl, or R$^{14}$ and R$^{15}$ together form —(CH$_2$)$_k$— wherein k=4, 5 or 6, wherein alkyl represents a non-cyclic hydrocarbon radical which is straight-chain or branched and is saturated or unsaturated and is unsubstituted or is monosubstituted or polysubstituted by identical or different substituents, cycloalkyl represents an alicyclic hydrocarbon radical which is saturated or unsaturated and is unsubstituted or is monosubstituted or polysubstituted by identical or different substituents, aryl is a radical selected from the group comprising

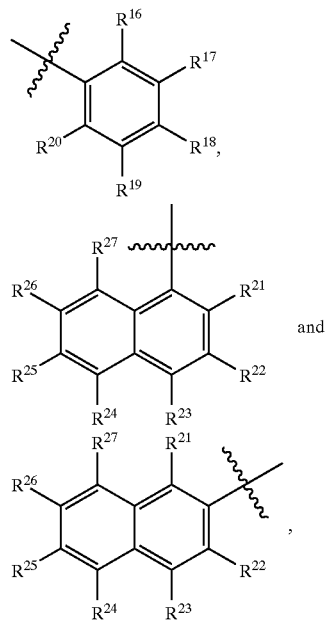

and heterocyclyl represents a monocyclic or polycyclic organic radical in which at least one ring contains one hetero atom or 2, 3, 4 or 5 identical or different hetero atoms selected from the group containing N, O and S, the radical being saturated or unsaturated and being unsubstituted or monosubstituted or polysubstituted by identical or different substituents, R$^{16}$, R$^{17}$, R$^{18}$, R$^{19}$, R$^{20}$, R$^{21}$, R$^{22}$, R$^{23}$, R$^{24}$, R$^{25}$, R$^{26}$ and R$^{27}$ each independently of the others represents H, OR$^{28}$, S(O)$_t$R$^{29}$ wherein t=0, 1 or 2, SO$_2$OR$^{30}$, F, Cl, Br, I, —CN, NO$_2$, C$_{1-12}$-alkyl, C$_{3-8}$-cycloalkyl, (C$_{1-6}$-alkyl)-C$_{3-8}$-cycloalkyl, phenyl or (C$_{1-6}$-alkyl)-phenyl, wherein phenyl is unsubstituted or is monosubstituted or polysubstituted by identical or different substituents, heterocyclyl, (C$_{1-6}$-alkyl)-heterocyclyl, —CO$_2$R$^{31}$ or —NR$^{32}$R$^{33}$, R$^{28}$, R$^{29}$, R$^{30}$ and R$^{31}$ each independently of the others represents H, C$_{1-12}$-alkyl, C$_{3-8}$-cycloalkyl, (C$_{1-6}$-alkyl)-C$_{3-8}$-cycloalkyl, phenyl or (C$_{1-6}$-alkyl)-phenyl, wherein phenyl is unsubstituted or is monosubstituted or polysubstituted by identical or different substituents, heterocyclyl, (C$_{1-6}$-alkyl)-heterocyclyl or —NR$^{34}$R$^{35}$, R$^{32}$ and R$^{33}$ each independently of the other represents H, C$_{1-6}$-alkyl, C$_{3-8}$-cycloalkyl, (C$_{1-6}$-alkyl)-C$_{3-8}$-cycloalkyl, phenyl, (C$_{1-6}$-alkyl)-phenyl, heterocyclyl or (C$_{1-6}$-alkyl)-heterocyclyl, or R$^{32}$ and R$^{33}$ together form —(CH$_2$)$_h$— wherein h=4, 5 or 6, and R$^{34}$ and R$^{35}$ each independently of the other represents H, C$_{1-6}$-alkyl, C$_{3-8}$-cycloalkyl, (C$_{1-6}$-alkyl)-C$_{3-8}$-cycloalkyl, phenyl, (C$_{1-6}$-alkyl)-phenyl, heterocyclyl or (C$_{1-6}$-alkyl)-heterocyclyl, or R$^{34}$ and R$^{35}$ together form —(CH2)$_g$— wherein g=4, 5 or 6, and a pharmaceutically acceptable excipient.

15. A method for treating pain, comprising administering a pharmaceutical composition of claim 14 to a patient in need thereof.

16. A method according to claim 15, wherein the patient is a mammal.

17. A method according to claim 16, wherein the mammal is a human.

18. A method for treating migraine, comprising administering a pharmaceutical composition of claim 14 to a patient in need thereof.

19. A method according to claim 18, wherein the patient is a mammal.

20. A method according to claim 19, wherein the mammal is a human.

* * * * *